United States Patent [19]

Stokbroekx et al.

[11] Patent Number: 5,196,535

[45] Date of Patent: Mar. 23, 1993

[54] INTERMEDIATES FOR PRODUCING ANTIPICORNAVIRAL PYRIDAZINAMINES

[75] Inventors: Raymond A. Stokbroekx, Beerse; Marcel G. M. Luyckx, Geel; Gilbert A. J. Grauwels, Kessel-Lo; Cyriel A. M. Van der Eycken, Vosselaar, all of Belgium

[73] Assignee: Janssen Pharmaceutica N.V., Beerse, Belgium

[21] Appl. No.: 789,563

[22] Filed: Nov. 8, 1991

Related U.S. Application Data

[60] Division of Ser. No. 618,775, Jan. 27, 1990, Pat. No. 5,100,893, which is a continuation-in-part of Ser. No. 510,635, Apr. 18, 1990, abandoned, which is a continuation-in-part of Ser. No. 456,395, Dec. 26, 1989, abandoned.

[51] Int. Cl.[5] .................................. C07D 271/06
[52] U.S. Cl. ................................. 546/209; 540/470; 540/480; 540/500; 540/519; 546/112; 544/253; 544/367; 544/369; 548/131 548/143; 548/235;
[58] Field of Search ............... 546/209; 544/369, 367; 540/480; 548/131, 143

[56] References Cited

U.S. PATENT DOCUMENTS 4,857,539 8/1989 Diana et al. .................. 548/131
4,992,433 2/1991 Stokbroekx et al. .......... 514/252
5,070,090 12/1991 Stokbroekx et al. .......... 514/252
5,100,893 3/1992 Stokbroekx et al. .......... 514/252

Primary Examiner—Donald C. Daus
Attorney, Agent, or Firm—Charles J. Metz

[57] ABSTRACT

Piperidinyl, pyrrolidinyl, azepinyl and piperazinyl pyridazines of formula

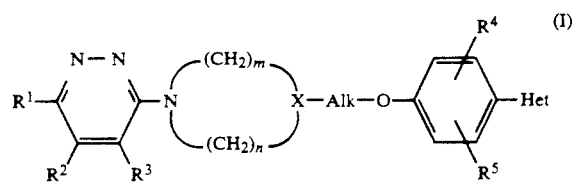

wherein one or two carbon atoms of the

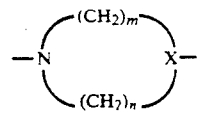

moiety may be substituted with $C_{1-4}$alkyl, $C_{1-4}$alkyloxy or two carbon atoms of the $CH_2$ groups of said moiety may be bridged with a $C_{2-4}$alkanediyl radical;
X represents CH or N; $R^1$ represents hydrogen, $C_{1-4}$alkyl, halo, hydroxy, trifluoromethyl, cyano, $C_{1-4}$alkyloxy, $C_{1-4}$alkylthio, $C_{1-4}$alkylsulfinyl, $C_{1-4}$alkylsulfonyl, $C_{1-4}$alkyloxycarbonyl, $C_{1-4}$alkylcarbonyl or aryl; $R^2$ and $R^3$ each independently represent hydrogen or $C_{1-4}$alkyl; Alk represents $C_{1-4}$alkanediyl; $R^4$ and $R^5$ each independently represent hydrogen, $C_{1-4}$alkyl or halo; and
Het represents

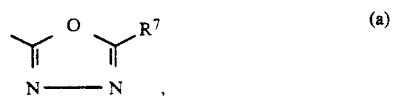 (a)

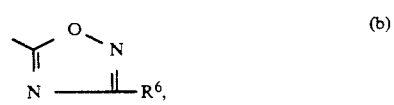

(b)

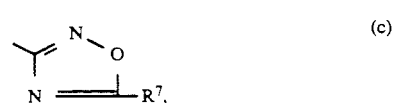

(c)

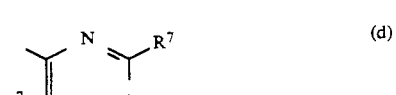

(d)

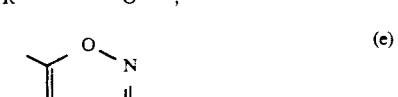

(e)

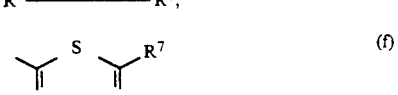

(f)

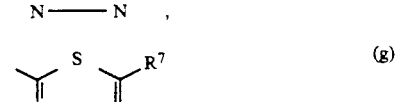

(g)

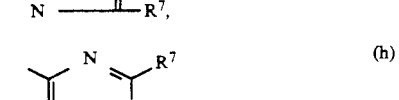

(h)

the addition salts and stereochemically isomeric forms thereof, said compounds having antipicornaviral activity. Pharmaceutical compositions containing these compounds as active ingredient, and a method of preparing said compounds and pharmaceutical compositions.

8 Claims, No Drawings

INTERMEDIATES FOR PRODUCING ANTIPICORNAVIRAL PYRIDAZINAMINES

CROSS-REFERENCE TO RELATED APPLICATIONS

This application is a division of application Ser. No. 618,775, filed Nov. 27, 1990, now U.S. Pat. No. 5,100,893, which was a continuation-in-part of application Ser. No. 510,635, filed Apr. 18, 1990, now abandoned, which was a continuation-in-part of application Ser. No. 456,395, filed on Dec. 26, 1989, now abandoned.

BACKGROUND OF THE INVENTION

EP-A-0,156,433 and EP-A-0,320,032 describe antivirally active pyridazinamines. Further antiviral agents are disclosed in U.S. Pat. No. 4,451,476 and in EP-A-0,137,242 and EP-A-0,207,453.

The compounds of the present invention differ from the cited pyridazinamine compounds by the fact that they contain a phenoxy moiety which is substituted with an oxadiazolyl, thiadiazolyl, 1,3-oxazol-4-yl, thiazolyl or isoxazolyl ring and particularly by the fact that they have favourable antipicornaviral properties.

DESCRIPTION OF THE INVENTION

The present invention is concerned with novel pyridazinamines of formula

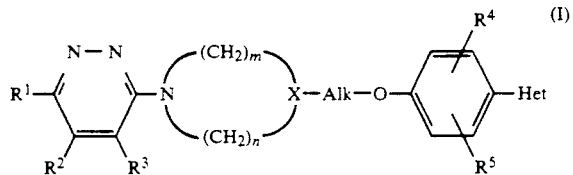

the acid addition salts and the stereochemically isomeric forms thereof, wherein
one or two carbon atoms of the CH$_2$ groups of the

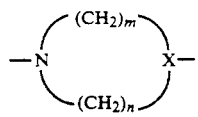

moiety may be substituted with C$_{1-4}$alkyl, C$_{1-4}$alkyloxy or two carbon atoms of the CH$_2$ groups of said moiety may be bridged with a C$_{2-4}$alkanediyl radical;
X represents CH or N;
m and n each independently represent 1, 2, 3 or 4, with the sum of m and n being 3, 4 or 5;
R$^1$ represents hydrogen, C$_{1-4}$alkyl, halo, hydroxy, trifluoromethyl, cyano, C$_{1-4}$alkyloxy, C$_{1-4}$alkylthio, C$_{1-4}$alkylsulfinyl, C$_{1-4}$alkylsulfonyl, C$_{1-4}$alkyloxycarbonyl, C$_{1-4}$alkylcarbonyl or aryl;
R$^2$ and R$^3$ each independently represent hydrogen or C$_{1-4}$alkyl;
Alk represents C$_{1-4}$alkanediyl;
R$^4$ and R$^5$ each independently represent hydrogen, C$_{1-4}$alkyl or halo; and
Het represents

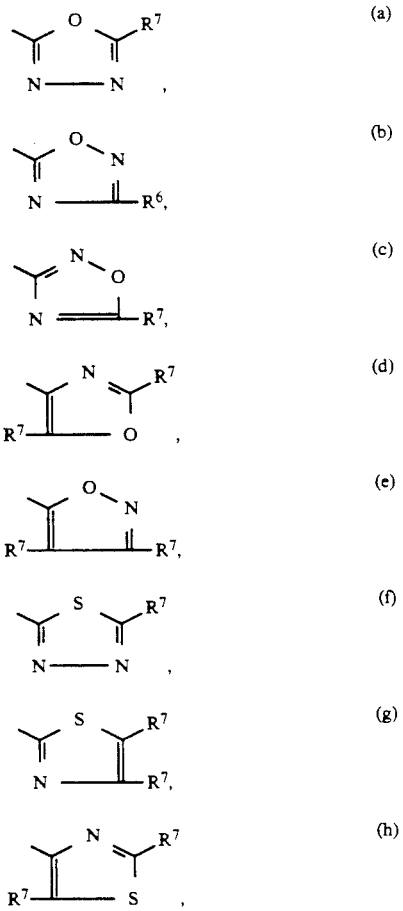

wherein R$^6$ represents hydrogen; C$_{1-6}$alkyl; hydroxyC$_{1-6}$alkyl; C$_{3-6}$cycloalkyl; aryl; arylC$_{1-4}$alkyl; C$_{1-4}$alkyloxyC$_{1-4}$alkyl; C$_{3-6}$cycloalkylC$_{1-4}$alkyl; trifluoromethyl or amino;
each R$^7$ independently represents hydrogen; C$_{1-6}$alkyl; C$_{3-6}$cycloalkyl; aryl; arylC$_{1-4}$alkyl; C$_{1-4}$alkyloxyC$_{1-4}$alkyl; C$_{3-6}$cycloalkylC$_{1-4}$alkyl or trifluoromethyl; and
each aryl independently represents phenyl or phenyl substituted with 1 or 2 substituents each independently selected from halo, C$_{1-4}$alkyl, trifluoromethyl, C$_{1-4}$alkyloxy or hydroxy.

As used in the foregoing definitions halo is generic to fluoro, chloro, bromo and iodo; C$_{1-4}$alkyl defines straight and branched chain saturated hydrocarbon radicals having from 1 to 4 carbon atoms such as, for example, methyl, ethyl, propyl, 1-methylethyl, butyl, 1,1-dimethylethyl and the like; C$_{1-6}$alkyl defines C$_{1-4}$alkyl radicals as defined hereinabove and the higher homologs thereof having 5 or 6 carbon atoms; C$_{3-6}$cycloalkyl defines cyclopropyl, cyclobutyl, cyclopentyl and cyclohexyl; C$_{1-4}$alkanediyl defines bivalent straight and branched chain hydrocarbon radicals having from 1 to 4 carbon atoms such as, for example, methylene, 1,2-ethanediyl, 1,3-propanediyl, 1,4-butanediyl and the branched isomers thereof. It is to be understood that in radicals (d), (e), (g) and (h), each R$^7$ can be the same or different. Typical examples of the

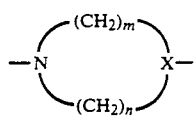

moiety are

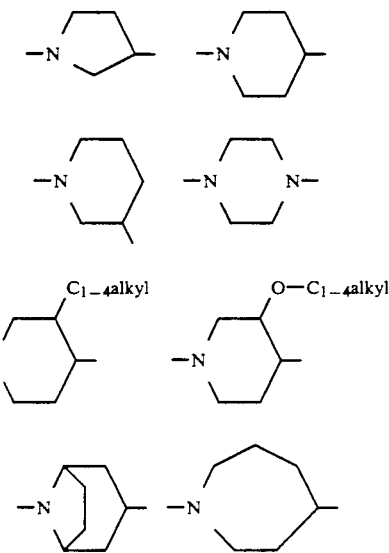

The pharmaceutically acceptable acid addition salts as mentioned hereinabove comprise the therapeutically active non-toxic acid addition salt forms which the compounds of formula (I) are able to form. Said salt forms can conveniently be obtained by treating the base form of the compounds of formula (I) with appropriate acids such as, inorganic acids, for example, hydrohalic acids, e.g. hydrochloric, hydrobromic and the like acids, sulfuric acid, nitric acid, phosphoric acid and the like; or organic acids such as, for example, acetic, hydroxyacetic, propanoic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form. The term acid addition salt also comprises the hydrates and solvent addition forms which the compounds of formula (I) are able to form. Examples of such forms are e.g. hydrates, alcoholates and the like.

The compounds of formula (I) may have asymmetric carbon atoms in their structure. The absolute configuration of these centres may be indicated by the stereochemical descriptors R and S. The relative configuration of two asymmetric centres may be indicated by the stereochemical descriptors cis and trans. Unless otherwise mentioned or indicated, the chemical designation of compounds denotes the mixture of all possible stereochemically isomeric forms, said mixtures containing all diastereomers and enantiomers of the basic molecular structure. Stereochemically isomeric forms, as well as mixtures thereof, are obviously intended to be embraced within the scope of the invention.

The compounds of formula (I) may contain in their structure a keto-enol tautomeric system, and consequently the compounds may be present in their keto form as well as their enol form. These tautomeric forms of the compounds of formula (I) are naturally intended to be embraced within the scope of the invention.

Particular compounds of formula (I) are those compounds wherein m is 1, 2 or 3 and n is 1 or 2 with the sum of m and n being 3, 4 or 5; and/or $R^1$ is hydrogen, $C_{1-4}$alkyl or halo; and/or $R^2$ and $R^3$ are both hydrogen; and/or $R^4$ and $R^5$ are each independently hydrogen or halo.

More particular compounds are those particular compounds wherein X is N; and/or in radicals (a), (b), (c) and (f) $R^6$ or $R^7$ is $C_{1-4}$alkyl, trifluoromethyl, phenyl, $C_{3-6}$cycloalkyl or amino or in radicals (d), (e), (g) and (h) one $R^7$ is $C_{1-4}$alkyl while the other $R^7$ is hydrogen or $C_{1-4}$alkyl.

Other more particular compounds are those particular compounds wherein X is CH; and/or in radicals (a), (b), (c) and (f) $R^6$ or $R^7$ is $C_{1-4}$alkyl, trifluoromethyl, phenyl, $C_{3-6}$cycloalkyl or amino or in radicals (d), (e), (g) and (h) one $R^7$ is $C_{1-4}$alkyl while the other $R^7$ is hydrogen or $C_{1-4}$alkyl.

Interesting compounds are those more particular compounds wherein X is N; and/or Alk is methanediyl, ethanediyl or propanediyl; and/or $R^1$ is methyl, chloro or bromo; and/or m and n are both 2; and/or $R^4$ and $R^5$ are both hydrogen and Het is a radical of formula (b) or (c) wherein $R^6$ or $R^7$ is ethyl.

Other interesting compounds are those more particular compounds wherein X is CH; and/or Alk is methanediyl, ethanediyl or propanediyl; and/or $R^1$ is methyl, chloro or bromo; and/or m is 1 or 2 and n is 2; and/or $R^4$ and $R^5$ are hydrogen or chloro and in radicals (a), (b), (c) and (f) $R^6$ or $R^7$ is ethyl or trifluoromethyl and in radicals (d), (e), (g) and (h) one $R^7$ is ethyl while the other $R^7$ is hydrogen or ethyl.

More interesting compounds are those interesting compounds wherein X is CH; and/or $R^1$ is methyl or chloro; and/or m and n are both 2; and/or $R^4$ and $R^5$ are hydrogen and in radicals (a), (b), (c) and (f) $R^6$ or $R^7$ is ethyl and in radicals (d), (e), (g) and (h) one $R^7$ is ethyl while the other $R^7$ is hydrogen.

Preferred compounds are those more particular compounds wherein X is CH; and/or the CH$_2$ groups of the

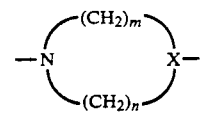

moiety are unsubstituted.

More preferred compounds are those preferred compounds wherein Alk is ethanediyl; and/or Het is a radical of formula (a) wherein $R^7$ is ethyl; or a radical of formula (b) wherein $R^6$ is methyl, ethyl or butyl; or a radical of formula (c) wherein $R^7$ is methyl, ethyl or propyl.

Other more preferred compounds are those preferred compounds wherein Alk is ethanediyl; and/or Het is a radical of formula (d) wherein one $R^7$ is ethyl or propyl while the other $R^7$ is hydrogen; or a radical of formula (e) wherein one $R^7$ is ethyl while the other $R^7$ is hydrogen; the radical (d) being particularly preferred.

Still other more preferred compounds are those preferred compounds wherein Alk is ethanediyl; and/or Het is a radical of formula (f) wherein $R^7$ is ethyl; or a radical of formula (g) wherein one $R^7$ is methyl or ethyl while the other $R^7$ is hydrogen or methyl; or a radical of formula (h) wherein one $R^7$ is ethyl while the other $R^7$ is hydrogen.

The most preferred compounds within the invention are selected from the group consisting of 3-[4-[2-[4-(3-ethyl-1,2,4-oxadiazol-5-yl)phenoxy]ethyl]-1-piperidinyl]-6-methylpyridazine, 3-[4-[2-[4-(5-ethyl-1,2,4-oxadiazol-3-yl)phenoxy]ethyl]-1-piperidinyl]-6-methylpyridazine, 3-methyl-6-[4-[2-[4-(3-methyl-1,2,4-oxadiazol-5-yl)phenoxy]ethyl]-1-piperidinyl]pyridazine, 3-[4-[2-[4-(2-ethyl-4-oxazolyl)phenoxy]ethyl]-1-piperidinyl]-6-methylpyridazine, and the pharmaceutically acceptable acid addition salts thereof.

In the following paragraphs, there are described different ways of preparing compounds of formula (I).

The compounds of formula (I) can generally be prepared by reacting an amine of formula (II) with a pyridazine of formula (III) following art-known N-alkylation procedures.

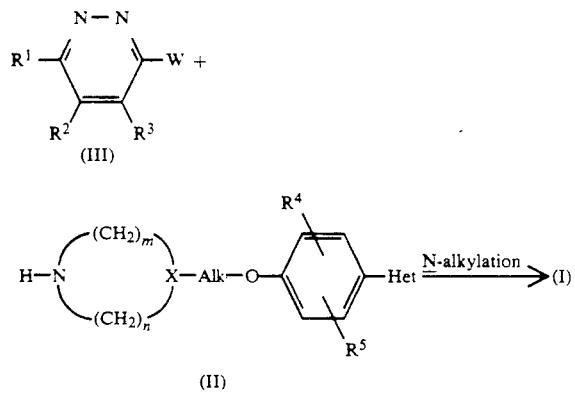

In the foregoing and following reaction schemes W represents an appropriate reactive leaving group such as, for example, halo, e.g. fluoro, chloro, bromo, iodo, or in some instances W may also be a sulfonyloxy group, e.g. 4-methylbenzenesulfonyl-oxy, benzenesulfonyloxy, 2-naphthalenesulfonyloxy, methanesulfonyloxy, trifluoromethanesulfonyloxy and the like reactive leaving groups.

The N-alkylation reaction can conveniently be carried out by mixing the reactants, optionally in a reaction-inert solvent such as, for example, water; an aromatic solvent, e.g. benzene, methylbenzene, dimethylbenzene, chlorobenzene, methoxybenzene and the like; a $C_{1-6}$alkanol, e.g. methanol, ethanol, 1-butanol and the like; a ketone, e.g. 2-propanone, 4-methyl-2-pentanone and the like; an ester, e.g. ethylacetate, γ-butyrolactone and the like; an ether, e.g. 1,1'-oxybisethane, tetrahydrofuran, 1,4-dioxane and the like; a dipolar aprotic solvent, e.g. N,N-dimethylformamide, N,N-dimethylacetamide, dimethylsulfoxide, pyridine, 1,3-dimethyl-3,4,5,6-tetrahydro-2(1H)-pyrimidinone, 1,3-dimethyl-2-imidazolidinone, 1,1,3,3-tetramethylurea, 1-methyl-2-pyrrolidinone, nitrobenzene, acetonitrile and the like; or a mixture of such solvents. The addition of an appropriate base such as, for example, an alkali metal or an earth alkaline metal carbonate, hydrogen carbonate, hydroxide, oxide, carboxylate, alkoxide, hydride or amide, e.g. sodium carbonate, sodium hydrogen carbonate, potassium carbonate, sodium hydroxide, calcium oxide, sodium acetate, sodium methoxide, sodium hydride, sodium amide and the like, or an organic base such as, for example, a tertiary amine, e.g. N,N-diethylethanamine, N-ethyl-N-(1-methylethyl)-2-propanamine, 4-ethylmorpholine, 1,4-diazabicyclo[2.2.2]octane, pyridene and the like, may optionally be used to pick up the acid which is formed during the course of the reaction. In some instances the addition of a iodide salt, preferably an alkali metal iodide, or a crown ether, e.g. 1,4,7,10,13,16-hexaoxacyclooctadecane and the like, may be appropriate. Stirring and somewhat elevated temperatures may enhance the rate of the reaction; more in particular the reaction may be conducted at the reflux temperature of the reaction mixture. Additionally, it may be advantageous to conduct said N-alkylation reaction under an inert atmosphere such as, for example, oxygen-free argon or nitrogen gas.

Alternatively, said N-alkylation reaction may be carried out by applying art-known conditions of phase transfer catalysis reactions. Said conditions comprise stirring the reactants, with an appropriate base and optionally under an inert atmosphere as defined hereinabove in the presence of a suitable phase transfer catalyst such as, for example, a trialkylphenylmethylammonium, tetraalkylammonium, tetraalkylphosphonium, tetraarylphosphonium halide, hydroxide, hydrogen sulfate and the like catalysts. Somewhat elevated temperatures may be appropriate to enhance the rate of the reaction.

In this and the following preparations, the reaction products may be isolated from the reaction mixture and, if necessary, further purified according to methodologies generally known in the art such as, for example, extraction, distillation, crystallization, trituration and chromatography.

The compounds of formula (I) can also be prepared by alkylating a phenol of formula (V) with a pyridazinamine derivative of formula (IV).

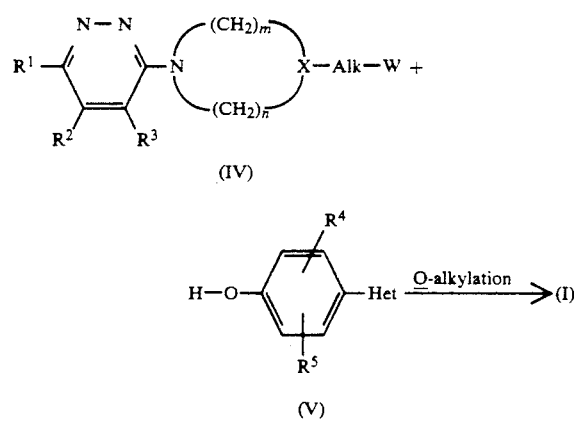

Said O-alkylation reaction can conveniently be carried out by mixing the reactants, optionally in a reaction-inert solvent such as, for example, water; an aromatic solvent, e.g. benzene, methylbenzene, dimethylbenzene and the like; a $C_{1-6}$alkanol, e.g. methanol, ethanol and the like; a ketone, e.g. 2-propanone, 4-methyl-2-pentanone and the like; an ester, e.g. ethylacetate, γ-butyrolactone and the like; an ether, e.g. 1,1'-oxybisethane, tetrahydrofuran, 1,4-dioxane and the like; a dipolar aprotic solvent, e.g. N,N-dimethylformamide, N,N-dimethylacetamide, dimethylsulfoxide and the like; or a mixture of such solvents. The addition of an appropriate base such as, for example, an alkali metal or an earth alkaline metal carbonate, hydrogen carbonate, hydroxide, oxide, carboxylate, alkoxide, hydride or amide, e.g. sodium carbonate, sodium hydrogen carbonate, potassium carbonate, sodium hydroxide, calcium oxide, sodium acetate, sodium methoxide, sodium hydride, sodium amide and the like, or an organic base such as, for example, a tertiary amine, e.g. N,N-diethylethanamine, N-ethyl-N-(1-methylethyl)-2-propanamine and the like, may optionally be used to pick up the acid which is formed during the course of the reaction. Further, it may be advantageous to convert the intermediate of formula (V) first into a suitable salt form thereof such as, for example, an alkali or earth alkaline metal salt, by reacting (V) with an appropriate base as defined hereinabove and subsequently using said salt form in the reaction with the alkylating reagent of formula (IV). Stirring and somewhat elevated temperatures may enhance the rate of the reaction; more in particular the reaction may be conducted at the reflux temperature of the reaction mixture. Additionally, it may be advantageous to conduct said alkylation reaction under an inert atmosphere such as, for example, oxygen-free argon or nitrogen gas.

Alternatively, said O-alkylation reaction may be carried out by applying art-known conditions of phase transfer catalysis reactions as described hereinbefore.

The compounds of formula (I) can alternatively be prepared by reacting a phenol of formula (V) with an alcohol of formula (VI) in the presence of a mixture of diethyl azodicarboxylate and triphenylphosphine.

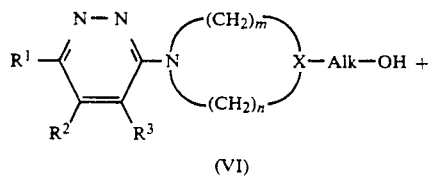

(VI)

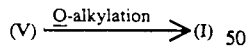

The reaction of (VI) with (V) can conveniently be conducted in an anhydrous reaction-inert solvent preferably under mild neutral conditions at room temperature or below. A suitable reaction-inert solvent is, for example, an aliphatic hydrocarbon, e.g. hexane and the like; an ether, e.g. 1,1'-oxybisethane, 2,2'-oxybispropane, tetrahydrofuran, 1,4-dioxane and the like; a dipolar solvent, e.g. hexamethylphosphoric triamide, N,N-dimethylformamide and the like or a mixture of such solvents.

The compounds of formula (I) may also be prepared by reacting an alcohol of formula (VI) with an appropriate reagent of formula (VII) according to the hereinbefore described O-alkylation procedures for the preparation of (I) from (IV) and (V).

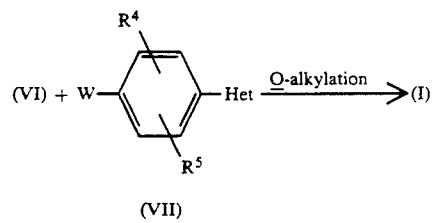

(VII)

The compounds of formula (I) wherein X is N said compounds being represented by (I-a), can also be prepared by N-alkylating a pyridazinamine of formula (VIII) with a reagent of formula (IX) following similar procedures as described hereinbefore for the preparation of (I) starting from (II) and (III).

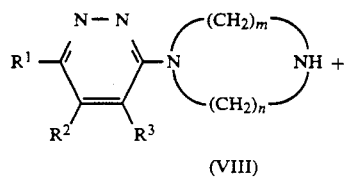

(VIII)

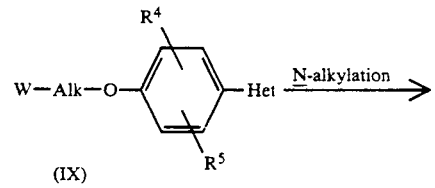

(IX)

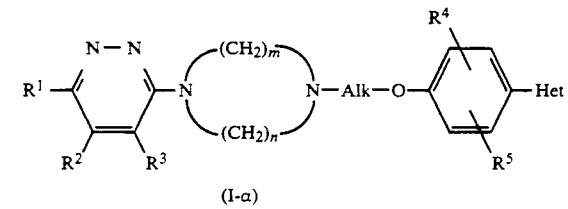

(I-a)

The compounds of formula (I-a) can also be prepared by reductively N-alkylating an intermediate of formula (VIII) with a ketone or aldehyde of formula (X) following "art-known reductive N-alkylation procedures".

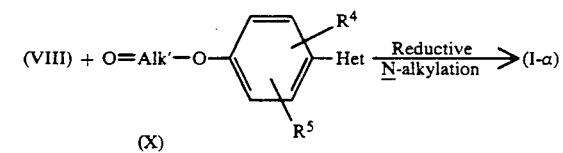

(X)

In formula (X) O=Alk'-represents a radical of formula H-Alk- wherein two geminal hydrogen atoms are replaced by oxygen.

Said reductive N-alkylation reaction may conveniently be carried out by reducing a mixture of the reactants in a suitable reaction-inert solvent. In particular, the reaction mixture may be stirred and/or heated in order to enhance the reaction rate. Suitable solvents are, for example, water; $C_{1-6}$alkanols, e.g. methanol, ethanol, 2-propanol and the like; esters, e.g. ethylacetate, γ-butyrolactone and the like; ethers, e.g. 1,4-dioxane, tetrahydrofuran, 1,1'-oxybisethane, 2-methoxyethanol and the like; halogenated hydrocarbons, e.g. dichloromethane, trichloromethane and the like; dipolar aprotic solvents, e.g. N,N-dimethylformamide, dimethyl sulfoxide and the like; carboxylic acids, e.g. acetic acid, propanoic acid and the like or a mixture of such solvents. The term "art-known reductive N-alkylation procedures" means that the reaction is carried out either with sodium cyanoborohydride, sodium borohydride, formic acid or a salt thereof, e.g. ammonium formate and the like reducing agents, or alternatively under a hydrogen atmosphere, optionally at an increased temperature and/or pressure, in the presence of an appropriate catalyst such as, for example, palladium-on-charcoal, platinum-on-charcoal and the like. In order to prevent the undesired further hydrogenation of certain functional groups in the reactants and the reaction products it may be advantageous to add an appropriate catalyst-poison to the reaction mixture, e.g., thiophene, quinoline-sulphur and the like. In some instances it also may be advantageous to add an alkali metal salt to the reaction mixture such as, for example, potassium fluoride, potassium acetate and the like salts.

Additionally the compounds of formula (I-α) may be prepared by cyclizing an intermediate of formula (XI) with an amine of formula (XII).

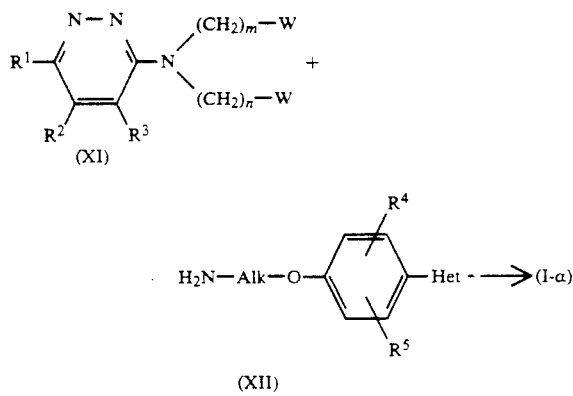

The reaction is carried out by stirring the reactants in an appropriate organic solvent such as, for example, 2-propanol, cyclohexanol, 2-propanone and the like, optionally in admixture with an appropriate polar solvent preferably at an elevated temperature. Addition to the reaction mixture of an appropriate base, such as, for example, an alkali or an earth alkaline metal carbonate, hydrogen carbonate or an organic base such as, for example, a tertiary amine, e.g. N,N-diethylethanamine may be suited to pick up the acid which is liberated during the course of the reaction. In order to enhance the rate of the reaction a small amount of an appropriate iodide salt, e.g. sodium or potassium iodide may be added.

Compounds of formula (I) wherein X is CH, said compounds being represented by formula (I-β), may also be prepared by reacting a ketone (XIII) with an ylide of formula (XV) or by reacting an aldehyde (XIV) with an ylide of formula (XVI) in a reaction-inert solvent, following art-known Wittig reaction procedures ($R^8$ and $R^9$ are aryl or $C_{1-6}$alkyl) or Horner-Emmons reaction procedures ($R^8$ is alkyloxy and $R^9$ is O−). Appropriate solvents are, for example, hydrocarbons, e.g. hexane, heptane, cyclohexane and the like; ethers, e.g. 1,1'-oxybisethane, tetrahydrofuran, 1,2-dimethoxyethane and the like; dipolar aprotic solvents, e.g. dimethylsulfoxide, hexamethylphosphor triamide, and the like. Then the unsaturated intermediates (XVII) and (XVIII) can be reduced following an appropriate reduction procedure, for example, by stirring and, if desired, heating the unsaturated intermediates in a suitable reaction-inert solvent in the presence of hydrogen and an appropriate catalyst such as, for example, palladium-on-charcoal and the like catalysts. Suitable solvents are alkanols, e.g. methanol, ethanol and the like, and carboxylic acids, e.g. acetic acid and the like.

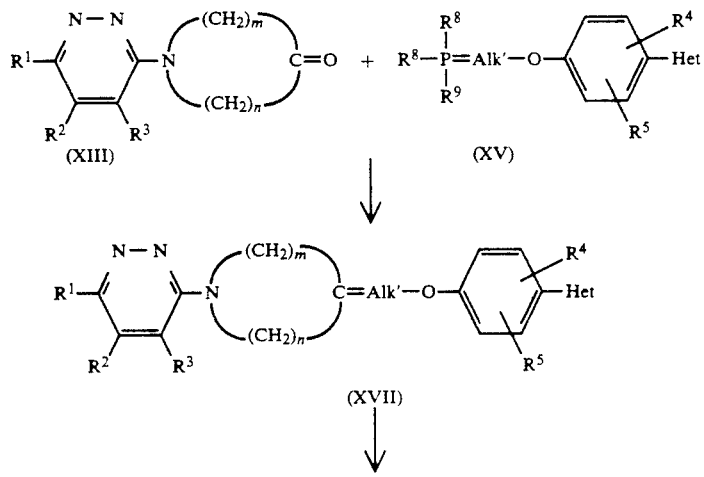

-continued

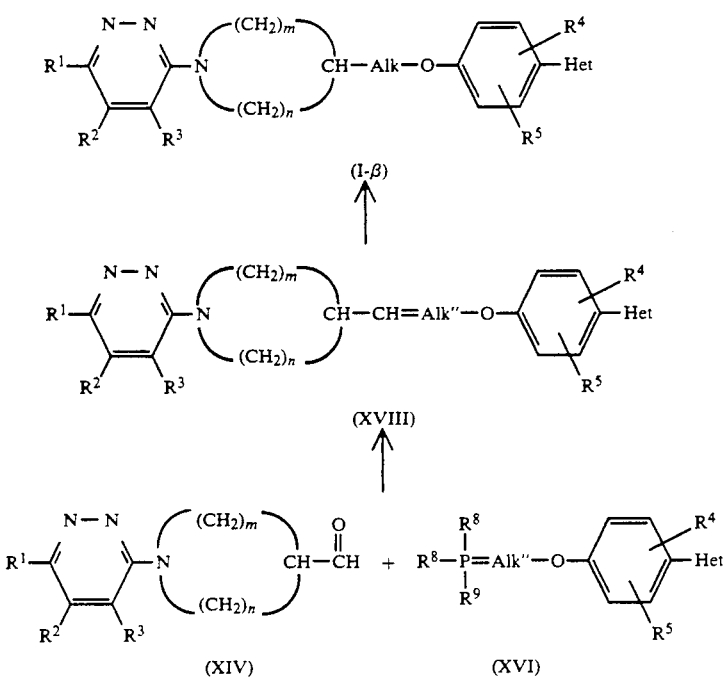

The intermediate ylides of formulae (XV) and (XVI) can be obtained by treating a phosphonium salt or a phosphonate with an appropriate base such as, for example, potassium tert. butoxide, methyllithium, butyllithium, sodium amide, sodium hydride, sodium alkoxide and the like bases under an inert atmosphere and in a reaction-inert solvent such as, for example, an ether, e.g. tetrahydrofuran, 1,4-dioxane and the like.

In (XV) $(R^8)_2R^9P=Alk'$- represents a radical of formula H-Alk- wherein two geminal hydrogen atoms are replaced by $(R^8)_2R^9P=$.

In (XVI) Alk" has the same meaning as Alk' with the proviso that one methylene is lacking.

Alternatively, the compounds of formula (I-$\beta$) may be prepared by reacting a ketone (XIII) with an organometallic reagent of formula (XIX), wherein M represents a metal group such as, for example, lithium, halo magnesium, copper lithium and the like, in a reaction-inert solvent such as, for example, an ether, e.g. tetrahydrofuran, 1,1'-oxybisethane, 1,2-dimethoxyethane and the like. The thus prepared alkanol of formula (XX) may subsequently be dehydrated with, for example, thionyl chloride in a suitable solvent like ethyl acetate or with an appropriate acid, e.g. hydrochloric or sulfuric acid, and hydrogenated to a compound of formula (I-$\beta$) following the procedure described hereinbefore for reducing an intermediate of formula (XVII) to a compound (I-$\beta$).

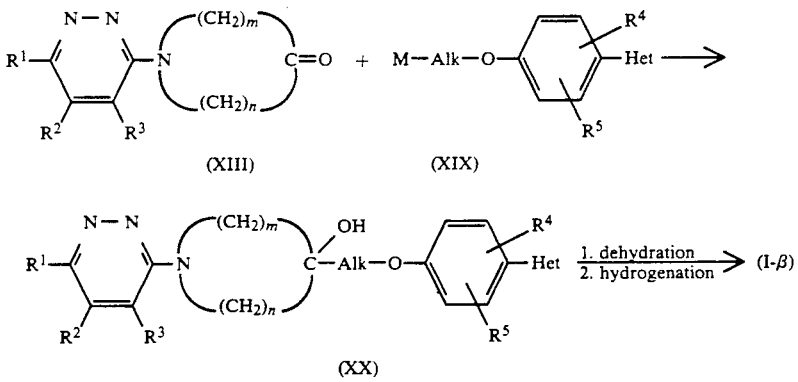

In a similar manner an aldehyde of formula (XIV) may also be reacted with an organometallic reagent, dehydrated and reduced to yield a compound of formula (I-$\beta$).

The compounds of the invention may also be prepared by construction of the Het ring from intermediates having a cyano, carbonyl or hydrazide group on the phenoxy moiety.

The compounds of formula (I) wherein Het is a 1,3,4-oxadiazol-2-yl (Y=O) of formula (a) or a 1,3,4-thiadiazol-2-yl (Y=S) of formula (f) can be prepared by condensing a reactive hydrazide of formula (XXI-a) or (XXI-f) with an ortho ester of formula (XXII).

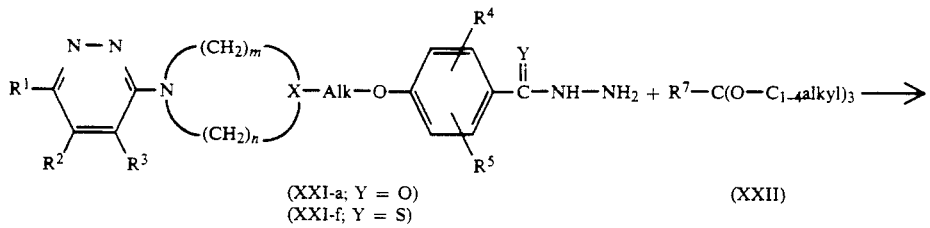

(XXI-a; Y = O)
(XXI-f; Y = S)      (XXII)

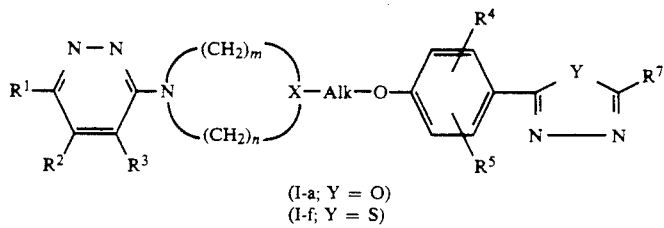

(I-a; Y = O)
(I-f; Y = S)

The compounds of formula (I) wherein Het is a 1,2,4-oxadiazol-5-yl-ring of formula (b), said compounds being represented by formula (I-b) can be prepared by reacting an intermediate of formula (XXI-b), wherein $R^{10}$ is hydrogen or $C_{1-4}$alkyl, with an amidoxime of formula (XXIII).

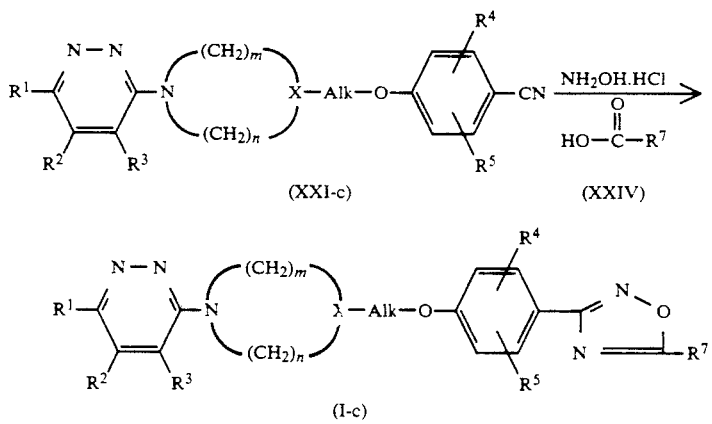

(XXI-b)      (XXIII)

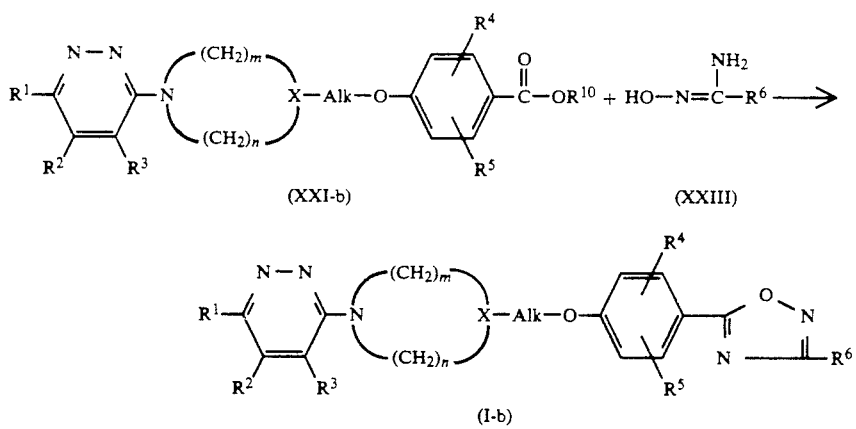

(I-b)

The compounds of formula (I) wherein Het is a 1,2,4-oxadiazol-3-yl ring of formula (c), said compounds being represented by formula (I-c) can be prepared by reacting an intermediate of formula (XXI-c) with hydroxylamine or an acid addition salt thereof and reacting the thus formed amidoxime with a carboxylic acid of formula (XXIV) or a functional derivative thereof, such as, for example, a halide, an anhydride or an ortho ester form thereof.

The condensation reactions to prepare compounds (I-a), (I-f), (I-b) and (I-c) can be carried out by stirring and if desired heating the intermediate starting materials, with or without a suitable reaction-inert solvent optionally in the presence of an appropriate base such as, a tertiary amine, an alkoxide, hydride or amide, e.g. pyridine, sodium methoxide, sodium ethoxide, sodium hydride or sodium amide. Suitable solvents for said condensation reactions are for example, ethers, e.g. 1,1′-oxybisethane, tetrahydrofuran, 1,4-dioxane, 1,2-dimethoxyethane and the like; alkanols, e.g. methanol, ethanol, propanol, butanol and the like; or mixtures of such solvents. The water or hydrohalic acid which is liberated during the condensation may be removed from the reaction mixture by azeotropical destillation, complexation, salt formation and the like methods.

The compounds of formula (I) can also be converted into each other following art-known functional group transformation procedures.

The compounds of formula (I) containing an ester group may be converted into the corresponding carboxylic acids following art-known saponification procedures, e.g. by treating the starting compound with an aqueous alkaline or an aqueous acidic solution. Said carboxylic acids can further be converted into the corresponding acyl halides by treatment with a suitable halogenating agent such as, for example, thionyl chloride, pentachlorophosphorane and sulfuryl chloride. The acyl halides can be converted into aldehydes by reduction with hydrogen in the presence of a catalyst like, for example, palladium-on-charcoal. Said aldehydes can be further reduced to alcohols with, for example, hydrogen in the presence of a catalyst such as Raney nickel.

A number of intermediates and starting materials in the foregoing preparations are known compounds which may be prepared according to art-known methodologies. Some intermediates are new and are especially developped for the preparation of the compounds of formula (I), such as, for example, the intermediates of formula (II) and some of the intermediates of formula (V). A number of the preparation methods, in particular for said novel intermediates, is described hereinafter in more detail.

In the next reaction scheme there are described some different ways of preparing intermediates of formula (II). In some instances it may be advantageous to protect the free nitrogen atom of the starting materials of formulae (XXV), (XXVI), (XXVII), (XXVIII), (XXIX) and (XXX) used for the preparation of intermediates of formula (II) as described hereinafter. Especially for the intermediates of formula (XXV), (XXVI), (XXIX) and (XXX) the protective group is important. Preferred protective groups may be, for example, hydrogenolyzable groups, e.g. phenylmethyl, phenylmethoxycarbonyl and the like, or hydrolyzable groups, e.g. $C_{1-4}$alkylcarbonyl, $C_{1-4}$alkylphenylsulfonyl and the like.

The intermediates of formula (II) can be prepared by O-alkylating a phenol of formula (V) with a reagent of formula (XXV), by reacting a phenol (V) with an alcohol of formula (XXVI) or alternatively by O-alkylating an alcohol of formula (XXVI) with an appropriate reagent of formula (VII), following the same methods as described hereinbefore for the preparation of (I).

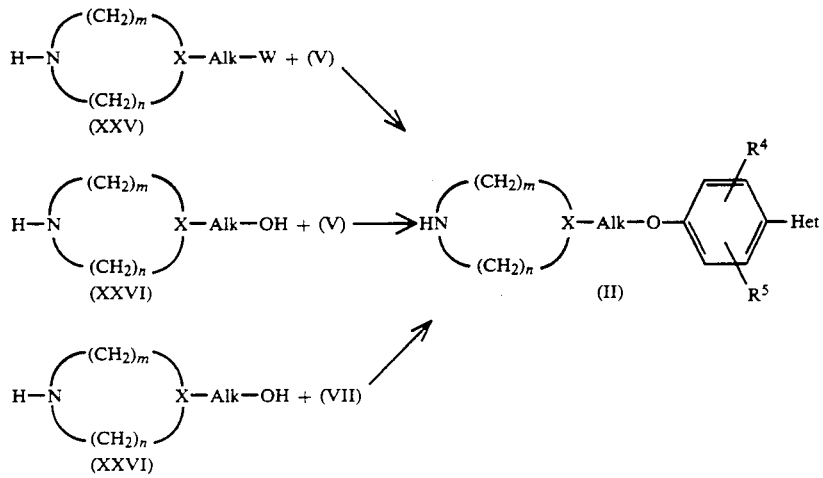

The intermediates of formula (II) wherein X is N, said intermediates being represented by (II-a), can be prepared by N-alkylating an amine of formula (XXVII) with a reagent of formula (IX), following N-alkylation procedures as described hereinbefore.

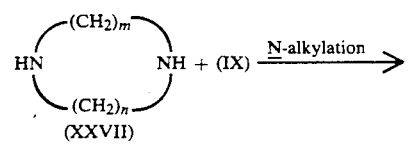

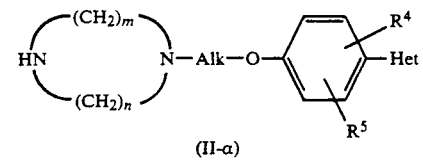

The intermediates of formula (II-a) can alternatively be prepared by reductive N-alkylating an intermediate of formula (XXVII) with a ketone or aldehyde of formula (X) following art-known N-alkylation procedures as described hereinbefore for the synthesis of (I-a) starting from (VIII) and (X).

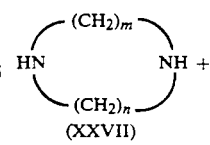

-continued

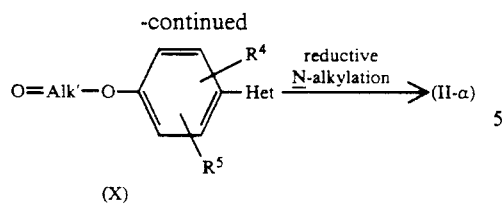
(X)

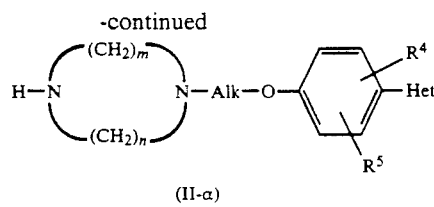
(II-α)

Additionally the intermediates of formula (II-α) may be prepared by cyclizing an intermediate of formula (XXVIII) with an amine of formula (XII) as described hereinbefore for the preparation of (I-α) from (XI) and (XII).

Intermediates of formula (II) wherein X is CH, said intermediates being represented by formula (II-β), may also be prepared by reacting a ketone of formula (XXIX) with an ylide of formula (XV) or by reacting an aldehyde (XXX) with an ylide of formula (XVI). Reduction of the thus obtained intermediates yields intermediates of formula (II-β) as described hereinbefore for the preparation of (I-β).

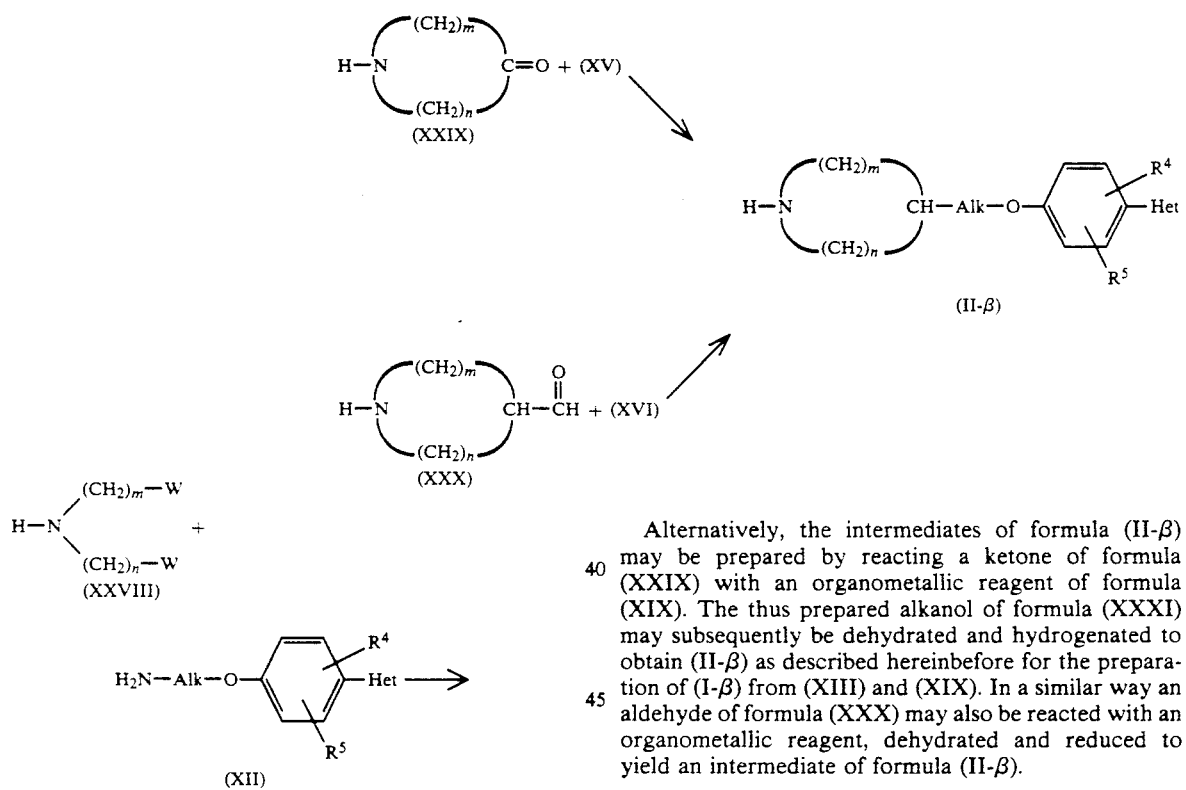

Alternatively, the intermediates of formula (II-β) may be prepared by reacting a ketone of formula (XXIX) with an organometallic reagent of formula (XIX). The thus prepared alkanol of formula (XXXI) may subsequently be dehydrated and hydrogenated to obtain (II-β) as described hereinbefore for the preparation of (I-β) from (XIII) and (XIX). In a similar way an aldehyde of formula (XXX) may also be reacted with an organometallic reagent, dehydrated and reduced to yield an intermediate of formula (II-β).

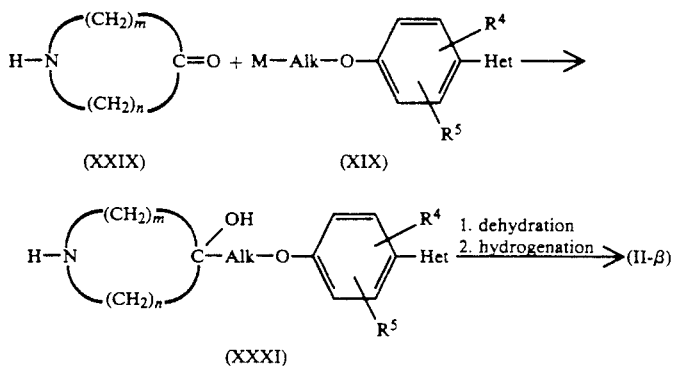

In these intermediates of formula (II) wherein the free nitrogen atom is protected, said protective group can be removed by hydrogenolysis, e.g. by treatment under a hydrogen atmosphere in a reaction-inert solvent in the presence of a hydrogenation catalyst such as palladium-on-charcoal, platinum-on-charcoal and the like; or by hydrolysis in an acidic or basic aqueous medium optionally in admixture with a co-solvent such as an alkanol, e.g. methanol, ethanol and the like.

Intermediates of formula (IV) can be prepared by N-alkylating an amine of formula

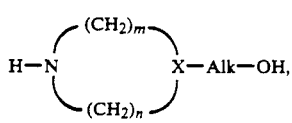
(XXVI), with a pyridazine of formula (III) following art-known N-alkylation procedures and subsequently converting the alcohol function of the thus obtained intermediate (VI) into an appropriate leaving group with an appropriate halogenating agent such as, for example, thionyl chloride, sulfuryl chloride, pentachlorophosphorane, pentabromophosphorane or an appropriate sulfonyl halide such as, for example, methanesulfonyl chloride or 4-methylbenzenesulfonyl chloride.

Intermediates of formula (II) and (V) may also be prepared by building up the Het ring from the corresponding intermediates having a cyano, carboxyl or hydrazide group according to similar cyclizing procedures as described hereinbefore for the synthesis of (I-a), (I-b), (I-c) and (I-f). In some instances it may be desired to protect the hydroxylgroup or aminomoiety of the starting compounds during the ring closure reaction with an appropriate protective group. For the intermediates of formula (V) the preparation is described hereinafter.

Intermediates of formula (V) wherein Het is a 1,3,4-oxadiazole-2-yl (Y=O) of formula (a) or a 1,3,4-thiadiazol-2-yl (Y=S) of formula (f) can be prepared by condensing a reactive hydrazide of formula (XXXII) with an ortho ester of formula (XXII) as described hereinbefore for the preparation of (I-a) and (I-f).

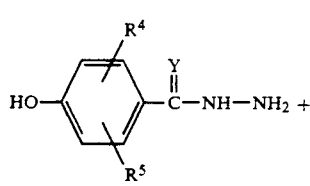

(XXXII-a; Y = O)
(XXXII-f; Y = S)

R$^7$—C(O—C$_{1-4}$alkyl)$_3$ ⟶
(XXII)

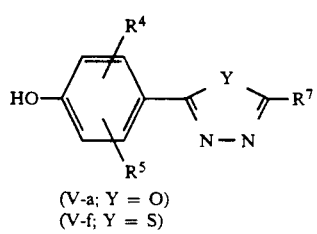

(V-a; Y = O)
(V-f; Y = S)

The intermediates of formula (V) wherein Het is a 1,2,4-oxadiazol-5-yl ring of formula (b), said intermediates being represented by formula (V-b), can be prepared by reacting an intermediate of formula (XXXIII), wherein R$^{10}$ is hydrogen or C$_{1-4}$alkyl, with an amidoxime of formula (XXIII). The reaction can be carried out as described hereinbefore for the preparation of (I-b).

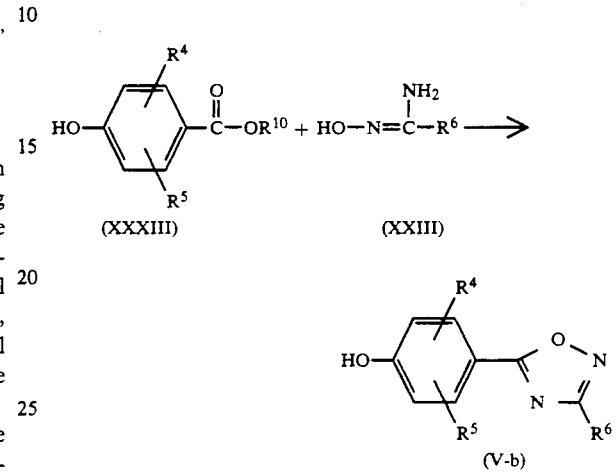

The intermediates of formula (V) wherein Het is a 1,2,4-oxadiazol-3-yl of formula (c), said intermediates being represented by formula (V-c), can be prepared by reacting an intermediate of formula (XXXIV) with hydroxylamine or an acid addition salt thereof and reacting the thus formed amidoxime with a carboxylic acid of formula (XXIV) or a funcional derivative thereof, such as, for example, a halide, an anhydride or an ortho ester form thereof. The reaction can be carried out as described hereinbefore for the preparation of (I-c).

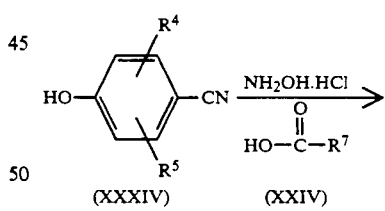

(XXXIV)    (XXIV)

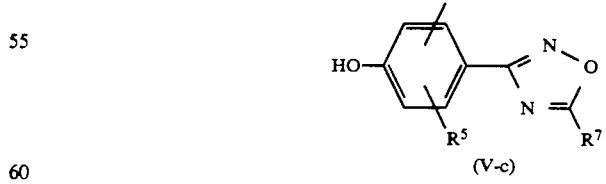

(V-c)

The intermediates of formula (V) wherein Het is a 1,3-oxazol-4-yl of formula (d), said intermediates being represented by formula (V-d), can be prepared by reacting an intermediate of formula (XXXV) with an ammonium salt of formula (XXXVI) in the presence of an acid such as, for example, acetic acid.

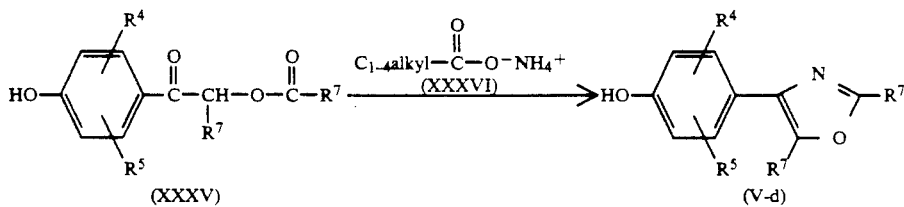

The intermediates of formula (V) wherein Het is a 1,3-oxazol-4-yl of formula (f) or a 1,3-thiazol-4-yl of formula (h), can be prepared by reacting an intermediate of formula (XXXVII) with a (thio)amide of formula (XXXVIII) in a suitable reaction-inert solvent like an alcohol, e.g. ethanol. In formula (XXXVII) $W^1$ represents a reactive leaving group such as halo, e.g., chloro, bromo and the like.

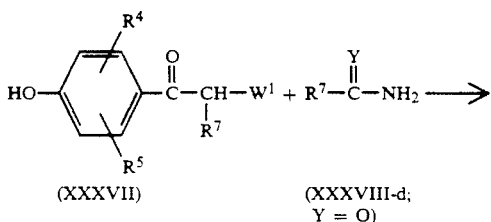

Finally, the intermediates of formula (V) wherein Het is a 1,3-thiazol-2-yl of formula (g) can be prepared by reacting a thioamide of formula (XXXIX) with a ketoderivative of formula (XXXX). The reaction is carried out in a suitable reaction-inert solvent like an alcohol, e.g. ethanol.

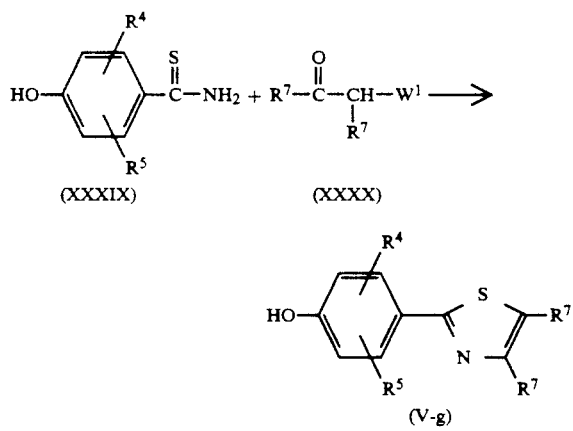

The intermediates of formula (VIII) can be obtained by reacting intermediates of formula (XXVII) with a pyridazine of formula (III) following art-known N-alkylation procedures as described hereinbefore.

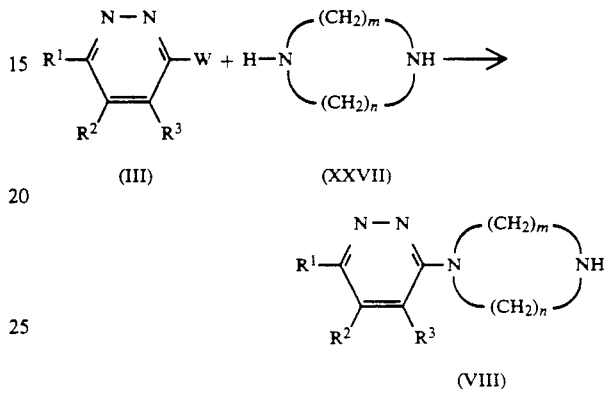

The intermediates can also be converted into each other following art-known procedures of functional group transformation as described hereinbefore for the compounds of formula (I).

Pure stereochemically isomeric forms of the compounds of this invention may be obtained by the application of art-known procedures. Diastereoisomers may be separated by physical separation methods such as selective crystallization and chromatographic techniques, e.g. counter current distribution, liquid chromatography and the like; and enantiomers may be separated from each other following art-known resolution methods, for example, by the selective crystallization of their diastereomeric salts with chiral acids.

Pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereoselective methods of preparation. These methods will advantageously employ enantiomerically pure starting materials.

The compounds of formula (I) and the pharmaceutically acceptable addition salts and stereoisomeric forms show antiviral activity and are particularly attractive due to their favourable therapeutic index, resulting from an acceptable low degree of cell toxicity, combined with satisfactory antiviral activity. The antiviral properties of the compounds of formula (I) can be demonstrated for example in the "Picornavirus Minimal Inhibitory Concentration (MIC)"-test, illustrating the useful antiviral activity of the compounds of the present invention.

The compounds of the present invention are therefore useful agents for inhibiting the replication of viruses. The compounds of formula (I), the pharmaceutically acceptable addition salts and stereochemically isomeric forms thereof are active against a broad spectrum of picornaviruses, including enteroviruses e.g. Polioviruses, Coxsackieviruses, Echoviruses, Enteroviruses, e.g. Enterovirus 70 and especially against numerous strains of rhinoviruses, e.g. Human Rhinovirus serotypes HRV -2, -3, -4, -5, -6, -9, -14, -15, -29, -39, -51, -59, -63, -70, -72, -85, -86 and the like. A number of compounds are also active against serotype HRV-45, a particular tenacious strain of rhinoviruses.

A noteworthy advantage of the compounds of the present invention is that they are less rapidly metabolized than the prior art compounds. Consequently, an effective antiviral concentration of said compounds can be sustained substantially longer at the site of application.

In view of their potent, local as well as systemic, antiviral activity the compounds of this invention constitute useful tools for inhibiting, combating or preventing the replication of viruses. More particularly there is provided a method of treating viral diseases in warm-blooded animals suffering from said viral diseases, especially respiratory diseases e.g. common cold, pneumonia, bronchiolitis, herpangina and the like, CNS-diseases e.g. paralysis, aseptic meningitis, encephalitis and the like, cardiac disease e.g. pericarditis, myocarditis and the like, hepatic diseases e.g. hepatitis and the like, gastrointestinal diseases e.g. diarrhea and the like, ophtalmic diseases e.g. acute hemorrhagic conjunctivitis and the like, dermatological diseases e.g. exanthem, rash, hand-foot-and-mouth disease, and the like diseases. Said method comprises the systemic or topical administration to warm-blooded animals of an antivirally effective amount of a compound of formula (I), a pharmaceutically acceptable addition salt or a stereoisomeric form thereof. Some compounds of the invention are especially useful to treat respiratory diseases, like common cold due to their prolonged in vivo activity in the buccal and nasal cavity. Further there is provided a method of treating viral diseases in insects such as, for example, bees, silkworms, and the like.

The subject compounds may be formulated into various pharmaceutical forms for systemic or topical administration purposes. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, intranasally, by parenteral injection or for ophthalmic administration. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions can take the form of creams, lotions, aerosols and/or emulsions and can be included in a transdermal patch of the matrix or reservoir type as are conventional in the art for this purpose.

In the compositions suitable for topical administration the active ingredient will preferably be a semisolid such as a thickened composition such as salves, creams, gellies, ointments and the like which can be applied by a swab. Pharmaceutical composition suitable for topical administration may also be in form of drops, lotions or an aerosol. Suitable aerosol preparations may include solutions and solids in powder form, which may be in combination with a pharmaceutically acceptable carrier, such as an inert compressed gas. Addition salts of (I) due to their increased water solubility over the corresponding base form, are obviously more suitable in the preparation of aqueous compositions.

In a further aspect of the invention there are provided particular pharmaceutical compositions which comprise a compound of formula (I), a pharmaceutically acceptable addition salt or a stereochemically isomeric form thereof and a cyclodextrin or a derivative thereof. When applied to the site of infection such cyclodextrin based compositions result in a continuous and controlled delivery of sufficiently high concentrations of the antiviral compound of formula (I) to the site of the infection for sustained periods of time.

Such compositions are particularly convenient for treating local viral infections, in particular mucosal infections, e.g. nasal or eye infections.

The cyclodextrin to be used in the aforementioned compositions include the pharmaceutically acceptable unsubstituted and substituted cyclodextrins known in the art, more particularly $\alpha$, $\beta$ or $\gamma$-cyclodextrins or the pharmaceutically acceptable derivatives thereof.

Substituted cyclodextrins which can be used in the invention include polyethers described in U.S. Pat. No. 3,459,731 which is incorporated by reference for the definition and processes for preparation. In general, unsubstituted cyclodextrins are reacted with an alkylene oxide, preferably under superatmospheric pressure and at an elevated temperature, in the presence of an alkaline catalyst.

Since a hydroxy moiety of the cyclodextrin can be substituted by an alkylene oxide which itself can react with yet another molecular of alkylene oxide, the average molar substitution (MS) is used as a measure of the average number of moles of the substituting agent per glucose unit. The MS can be greater than 3 and theoretically has no limit.

Further substituted cyclodextrins are ethers wherein the hydrogen of one or more cyclodextrin hydroxy groups is replaced by $C_{1-6}$alkyl, hydroxy$C_{1-6}$alkyl, carboxy$C_{1-6}$alkyl or $C_{1-6}$alkyloxycarbonyl$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxymethyl or carboxyethyl. In the foregoing definitions the term "$C_{1-6}$alkyl" is meant to include straight and branched saturated hydrocarbon radicals, having from 1 to 6 carbon atoms, such as, methyl, ethyl, 1-methylethyl, 1,1-dimethylethyl, propyl, 2-methylpropyl, butyl, pentyl, hexyl and the like.

Such ethers can be prepared by reacting the starting cyclodextrin with an appropriate O-alkylating agent or a mixture of such agents in a concentration being selected so that the desired cyclodextrin ether is obtained. The said reaction is preferably conducted in a suitable solvent in the presence of an appropriate base. With such ethers, the degree of substitution (DS) is the average number of substituted hydroxy functions per glucose unit, the DS being thus 3 or less.

In the cyclodextrin derivatives for use in the compositions according to the present invention, the DS preferably is in the range of 0.125 to 3, in particular 0.3 to 2, more in particular 0.3 to 1 and the MS is in the range of 0.125 to 10, in particular of 0.3 to 3 and more in particular 0.3 to 1.5.

Other references describing cyclodextrins for use in the compositions according to the present invention, and which provide a guide for the preparation and characteristics of cyclodextrins, for the process of depositing the selected agent within the cavity of the cyclodextrin molecule and for the use of cyclodextrins in pharmaceutical compositions, include the following:

"Cyclodextrin Technology" by József Szejtli, Kluwer Academic Publishers (1988) in the chapter Cyclodextrins in Pharmaceuticals; "Cyclodextrin Chemistry" by M. L. Bender et al., Springer-Verlag, Berlin (1978); "Advances in Carbohydrate Chemistry", Vol. 12 Ed. by M. L. Wolfrom, Academic Press, New York (157) in the chapter The Schardinger Dextrins by Dexter French at p. 189–260; "Cyclodextrins and their Inclusions Complexes" by J. Szejtli, Akademiai Kiado, Budapest, Hungary (1982); I. Tabushi in Acc. Chem. Research, 1982, 15, p. 66–72; W. Sanger, Angewandte Chemie, 92, p. 343–361 (1981); A. P. Croft and R. A. Bartsch in Tetrahedron, 39, p. 1417–1474 (1983); German Offenlegungsschrift DE 3,118,218; German Offenlegungsschrift DE 3,317,064; EP-A-0,094,157; EP-A-0,149,197; U.S. Pat. No. 4,659,696; and U.S. Pat. No. 4,383,992.

Of particular utility in the invention are the $\beta$-cyclodextrin ethers, e.g. dimethyl-$\beta$-cyclodextrin as described in Drugs of the Future, Vol. 9, No. 8, p. 577–578 by M. Nogradi (1984) and polyethers, e.g. hydroxypropyl $\beta$-cyclodextrin and hydroxyethyl $\beta$-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between $\beta$-cyclodextrin an propylene oxide and may have a MS value of about 0.125 to 10, e.g. about 0.3 to 3.

In said particular cyclodextrin based formulation, the molecules of the antiviral compounds of formula (I) are surrounded, at least in part, by the cyclodextrin, i.e. the agent fits into the cyclodextrin cavity.

To prepare said particular cyclodextrin based pharmaceutical compositions of the invention, the selected antiviral compound (or compounds) of formula (I), the pharmaceutically acceptable addition salt of the stereochemically isomeric form thereof is deposited within the cyclodextrin molecule itself, such process being known in the art for other active agents. In the final compositions, the molar ratio of cyclodextrin:antiviral compound is from about 1:1 to about 5:1, in particular, about 1:1 to about 2:1. Thus, in general, the composition will be prepared by dissolving the cyclodextrin in water and adding the antiviral compound to this solution, preferably under vigorous stirring and preferably at a temperature in the range of 10° C. to 50° C., in particular in range of 15° C. to 30° C., and preferably at room temperature.

In the final compositions, the amount of cyclodextrin will comprise about 2.5 to 40% by weight, in particular about 2.5% to 25%, more in particular 5 to 25%, or 5 to 20%, for example about 10%, the amount of active ingredient will range from about 0.001% to about 0.1% by weight, in particular from 0.005% to about 0.1% by weight, in particular from 0.005% to about 0.075%, more in particular from 0.01% to about 0.05%, for example about 0.025%, with the remainder being water, preservative and any excipients.

In particular, the pharmaceutical compositions may consist of water, cyclodextrin and the antiviral agents only, without the need for co-solvents such as ethanol or surfactants.

Application of the cyclodextrin based compositions of the invention may be by aerosol, e.g. with a propellant such as nitrogen, carbon dioxide, a freon, or without a propellant such as a pump spray, drops, or a semisolid such as a thickened compositions which can be applied by a swab. In particular applications, semisolid compositions such as salves, creams, gellies, ointments and the like will conveniently be used.

For the liquid preparations of said cyclodextrin based compositions, any of the usual pharmaceutical media may be added, such as, for example, glycols, oils, alcohols and the like, however in concentrations below the level of irritation. In order to stabilize the formulations the pH may be increased or decreased or stabilized by adding appropriate acids, bases or buffer systems, e.g. citrate, phosphate buffers. Further additives may comprise substances to make the formulations isotonic, e.g. sodium chloride, mannitol, glucose and the like. It is further recommendable to add a preservative to the formulations such as, for example, a mercury salt or complex salt, e.g. phenyl mercuriacetate, nitrate, chloride or borate, phenylethyl alcohol, ethanol, propylene glycol and the like. Suitable thickeners for obtaining the above-mentioned thickened compositions comprise polyvinyl alcohols, hydroxypropyl methyl celluloses, hydroxyethyl celluloses, methylcelluloses, polyvinyl pyrrolidone, acrylic acid polymers and the like.

Depending on the type of virus which is to be controlled, said cyclodextrin based compositions can be applied in the vagina, nose, mouth, eyes, lungs or within the cheeks so as to control viruses which have not entered the blood stream of the patient, e.g. viruses which are located in mucous membranes of the body. The cyclodextrin based compositions of the invention are particularly useful on those infection sites where the natural defense mechanisms prevent the delivery of antiviral agents during sustained periods due to an effective elimination of the active compound from the site of infection. Such elimination may be due to clearance by ciliary movement or secretion, or by absorption.

As part of the pharmaceutical composition, one may also include the same or a different active antiviral in a different delivery carrier so as to provide a different profile of activity, e.g. a wide range of time during which the composition shows activity or a supplement to bolster a low level at a particular point in the release schedule of the cyclodextrin.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, drops, teaspoonfuls, tablespoonfuls and the like, and segregated multiples thereof.

Those of skill in treating antiviral diseases in warm-blooded animals could easily determine the effective amount from the test results presented hereinafter. In general it is contemplated that an effective amount would be from 0.001 mg/kg to 50 mg/kg body weight, preferably from 0.01 mg/kg to 10 mg/kg body weight.

The following examples are intended to illustrate and not to limit the scope of the present invention in all its aspects. Unless otherwise stated all parts therein are by weight.

EXPERIMENTAL PART

A. Preparation of the intermediates

EXAMPLE 1 a) A mixture of 224 parts of piperazine, 97 parts of ethyl 4-(3-chloropropoxy)benzoate and 1044 parts of methylbenzene was stirred overnight at reflux temperature. After cooling, the reaction mixture was washed with water (3×), dried, filtered and evaporated, yielding 115.2 parts (98.5%) of ethyl 4-[3-(1-piperazinyl)-propoxy]benzoate (interm. 1). In a similar manner there was also prepared ethyl 4-[2-(1-piperazinyl)ethoxy]benzoate (interm. 2).

b) To a mixture of 1.6 parts of a sodium hydride dispersion in mineral oil (50%) and 71.2 parts of tetrahydrofuran there was added dropwise a solution of 2.64 parts of N-hydroxypropanimidamide in 22.3 parts of tetrahydrofuran. After stirring for 1 hour at room temperature, there was added dropwise a solution of 6.35 parts of intermediate 1 in 40.0 parts of tetrahydrofuran. Stirring was continued overnight at reflux temperature. After cooling, the reaction mixture was poured into ice-water. The product was extracted with dichloromethane and the extract was dried, filtered and evaporated, yielding 5.0 parts (79.0%) of 1-[3-[4-(3-ethyl-1,2,4-oxadiazol-5-yl)phenoxy]propyl]piperazine (interm. 3).

In a similar manner there were also prepared:
2,6-dichloro-4-(3-ethyl-1,2,4-oxadiazol-5-yl)phenol; mp. 173.3° C. (interm. 4) and
2-chloro-4-(3-ethyl-1,2,4-oxadiazol-5-yl)phenol; mp. 90.7° C. (interm. 5).

EXAMPLE 2

To a mixture of 29.9 parts of ethyl 4-hydroxybenzoate and 316 parts of ethanol there were added portionwise 35.6 parts of sodiumethoxide. After stirring for ½ hour at room temperature, there was added dropwise a solution of 31.7 parts of N-hydroxypropanimidamide in 79 parts of ethanol. Stirring was continued for ½ hour at room temperature and overnight at reflux temperature. The reaction mixture was evaporated and the residue was taken up in water. After neutralizing with acetic acid, the precipitate was filtered off and dried. It was purified by column chromatography (HPLC; silica gel; CH$_2$Cl$_2$/CH$_3$OH 99:1). The eluent of the desired fraction was evaporated and the residue was stirred in petroleumether. The precipitate was filtered off and dried, yielding 7.56 parts (22.1%) of 4-(3-ethyl-1,2,4-oxadiazol-5-yl)phenol; mp. 137.7° C. (interm. 6).

EXAMPLE 3

A mixture of 4.0 parts of N-hydroxypropanimidamide, 2.9 parts of sodiumethoxide, 94.8 parts of ethanol and 25.3 parts of molecular sieve was stirred for 15 min. at room temperature. There were added 7.5 parts of ethyl 4-[2-(4-piperidinyl)ethoxy]benzoate monohydrochloride and stirring was continued for 12 hours at reflux temperature. The cooled reaction mixture was filtered and the filtrate was evaporated. The residue was partitioned between water and dichloromethane. The organic layer was separated, dried, filtered and evaporated, yielding 6.5 parts (89.9%) of 4-[2-[4-(3-ethyl-1,2,4-oxadiazol-5-yl)phenoxy]ethyl]piperidine (interm. 7).

EXAMPLE 4

A mixture of 19 parts of 4-hydroxybenzoic acid hydrazide and 89.8 parts of 1,1,1-triethoxypropane was refluxed overnight. After cooling the precipitate was filtered off, washed with petroleumether and dried, yielding 23 parts (96.7%) of 4-(5-ethyl-1,3,4-oxadiazol-2-yl)phenol (interm. 8).

In a similar manner there was also prepared 4-(5-ethyl-1,3,4-thiadiazol-2-yl)phenol (interm. 9).

EXAMPLE 5

A mixture of 6.2 parts of N,4-dihydroxybenzenecarboximidamide and 44.6 parts of triethoxymethane was stirred overnight at reflux temperature. The reaction mixture was poured into water and the product was extracted with trichloromethane. The extract was dried, filtered and evaporated. The residue was purified by column chromatography (silica gel; CHCl$_3$/CH$_3$OH 99:1). The eluent of the desired fraction was evaporated, yielding 1.5 parts (23.1%) of 4-(1,2,4-oxadiazol-3-yl)phenol (interm. 10).

EXAMPLE 6

A mixture of 14.1 parts of 3,5-dichloro-N,4-dihydroxybenzenecarboximidamide, 6.5 parts of propanoylchloride and 98 parts of pyridine was stirred for 4 hours at reflux temperature. The reaction mixture was concentrated and the residue was partitioned between water and dichloromethane. The organic layer was separated and washed successively with water (2×) and NaCl (dil.). The combined aqueous layers were washed with dichloromethane and then filtered over diatomaceous earth. After acidifying with acetic acid, the precipitate was filtered off and taken up in dichloromethane. This solution was dried, filtered and evaporated. The residue was crystallized from a mixture of ethanol and water. The product was filtered off and dried in vacuo at 50° C., yielding 4.25 parts (25.6%) of 2,6-dichloro-4-(5- ethyl-1,2,4-oxadiazol-3-yl)phenol; mp. 125.7° C. (interm. 11).

EXAMPLE 7

A mixture of 6.2 parts of 2-(4-hydroxyphenyl)-2-oxoethyl propanoate, 2.7 parts of ammonium acetate and 52.5 parts of acetic acid was stirred for 6 hours at reflux temperature. An additional 2.7 parts of ammonium acetate were added and stirring was continued for 5 hours at reflux temperature and overnight at room temperature. The reaction mixture was poured into water and the precipitate was filtered off, yielding a first fraction of product. The aqueous layer was extracted with methylbenzene. The extract was dried, filtered and then combined with the first product fraction. The whole was dried, filtered and evaporated, yielding 3.8 parts (66.9%) of 4-(2-ethyl-4-oxazolyl)phenol (interm. 12).

In a similar manner there was also prepared 4-(2-propyl-4-oxazolyl)phenol (interm. 13).

EXAMPLE 8

A mixture of 4.6 parts of 4-hydroxybenzothioamide, 4.5 parts of 1-bromo-2-butanone and 79 parts of ethanol was stirred for 5 hours at reflux temperature. After cooling, the precipitate was filtered off and dried in vacuo at 50° C., yielding 5.6 parts (65.2%) of 4-(4-ethyl-2-thiazolyl)phenol hydrobromide (interm. 14).

In a similar manner there were also prepared:
4-(5-ethyl-2-thiazolyl)phenol (interm. 15) and
4-(4,5-dimethyl-2-thiazolyl)phenol hydrobromide; mp. 257.5° C. (interm. 16).

EXAMPLE 9

A mixture of 3.6 parts of propanethioamide, 8.6 parts of 2-bromo-1-(4-hydroxyphenyl)ethanone and 79 parts of ethanol was stirred for 7 hours at reflux temperature. The reaction mixture was concentrated to ¼ of its volume and 2,2'-oxybispropane was added to the residue. The precipitate was filtered off and taken up in water. After basifying with NH4OH, the product was extracted with dichloromethane. The extract was dried, filtered and evaporated, yielding 3.3 parts (40.2%) of 4-(2-ethyl-4-thiazolyl)-phenol (interm. 17).

EXAMPLE 10 a) To a stirred mixture of 175.4 parts of ethyl 4-piperidineacetate, 116.6 parts of sodium carbonate and 2250 parts of trichloromethane there were added dropwise 119.4 parts of ethyl chloroformate. After stirring for 4 hours at room temperature, the reaction mixture was diluted with 400 parts of water. The organic layer was separated, dried, filtered and evaporated, yielding 277 parts (100%) of ethyl 1-(ethoxycarbonyl)-4-piperidineacetate (interm 18).

b) A mixture of 168 parts of potassium hydroxide and 1000 parts of water was stirred at 10° C. After warming to room temperature, there were added 249.4 parts of intermediate 18 and 400 parts of ethanol. Stirring was continued overnight. The solvent was evaporated and the cooled residue was diluted with water and acidified with hydrochloric acid while keeping the temperature below 20° C. The product was extracted with dichloromethane (2×520 parts) and the combined extracts were washed with water, dried, filtered and evaporated. The residue was suspended in hexane (2×) and then solidified upon stirring in 2,2'-oxybispropane. The product was filtered off and dried, yielding 170.7 parts of 1-(ethoxycarbonyl)-4-piperidineacetic acid (interm. 19).

c) To 960 parts of thionyl chloride there were added 155.15 parts of intermediate 19 at 10° C. After stirring overnight at room temperature, the reaction mixture was evaporated. The residue was distilled, yielding 157 parts (93.3%) of ethyl 4-(2-chloro-2-oxoethyl)-1-piperidinecarboxylate; bp. 140°-145° C. at 133 Pa (interm. 20).

d) A mixture of 157 parts of intermediate 20; 75 parts of 2,6-dimethylpyridine and 1890 parts of tetrahydrofuran was hydrogenated at normal pressure and room temperature with 15 parts of palladium-on-charcoal catalyst 10%. After the calculated amount of hydrogen was taken up, the catalyst was filtered off and the filtrate was evaporated. The residue was dissolved in dichloromethane. This solution was washed with diluted hydrochloric acid (2×) and water, dried, filtered and evaporated. The residue was distilled, yielding 122.7 parts (91.6%) of ethyl 4-(2-oxoethyl)-1-piperidinecarboxylate; bp. 125°-130° C. at 133 Pa (interm. 21).

e) A mixture of 13.9 parts of intermediate 21;39.5 parts of methanol and 5 parts of potassium acetate was hydrogenated at normal pressure and at room temperature with 3 parts of Raney nickel. After the calculated amount of hydrogen was taken up, the catalyst was filtered off and the filtrate was evaporated. The residue was taken up in water and the product was extracted with methylbenzene. The extract was dried, filtered and evaporated, yielding 8.3 parts (58.9%) of ethyl 4-(2-hydroxyethyl)-1-piperidinecarboxylate (interm. 22).

f) A mixture of 8.3 parts of intermediate 22 and 176 parts of hydrochloric acid 35% was stirred for 1 hour at reflux temperature. The reaction mixture was evaporated, yielding 6.1 parts (89.8%) of 4-piperidineethanol hydrochloride (interm. 23).

EXAMPLE 11 a) A mixture of 6.1 parts of 3,6-dichloropyridazine, 6.8 parts of intermediate 23;21 parts of sodium carbonate and 188 parts of N,N-dimethylformamide was stirred overnight at 60° C. The reaction mixture was evaporated and the residue was partitioned between water and trichloromethane. The organic layer was dried, filtered and evaporated and the residue was purified by column chromatography (silica gel; CHCl3/CH3OH 97:3). The eluent of the desired fraction was evaporated, yielding 5.2 parts (52.5%) of 1-(6-chloro-3-pyridazinyl)-4-piperidineethanol (interm. 24).

In a similar manner there were also prepared:
1-(6-chloro-3-pyridazinyl)-4-piperidinepropanol (interm. 25);
1-(6-chloro-3-pyridazinyl)-4-piperidinemethanol (interm. 26);
ethyl 4-[2-[1-(6-methyl-3-pyridazinyl)-4-piperidinyl]ethoxy]benzoate; mp. 130.1° C. (interm. 27);
cis-1-(6-chloro-3-pyridazinyl)-3-methyl-4-piperidineethanol (interm. 28);
trans-1-(6-chloro-3-pyridazinyl)-3-methyl-4-piperidineethanol (interm. 29);
1-(6-chloro-3-pyridazinyl)-hexahydro-1H-azepine-4-ethanol (interm. 30)

Using a slightly changed preparation method there were also prepared:
1-(6-methyl-3-pyridazinyl)-4-piperidinepropanol; mp. 84.8° C. (interm. 31) (the mixture was stirred for 5 hours at 150° C.);

1-(6-methyl-3-pyridazinyl)-4-piperidineethanol; bp. 99°–100° C. at 8 Pa (interm. 32) (the mixture was stirred for 5 hours at 150° C.);

1-(6-methyl-3-pyridazinyl)-4-piperidinemethanol; mp. 120.1° C. (interm. 33) (the mixture was stirred for 5 hours at 150° C. in N,N-dimethylacetamide);

ethyl 4-[2-[4-(6-chloro-3-pyridazinyl)-1-piperazinyl]ethoxy]benzoate; mp. 132.9° C. (interm. 34) (the mixture was stirred for 7 hours at 140° C.).

b) To 5.1 parts of thionyl chloride there was added dropwise a solution of 5.2 parts of intermediate 24 in 133 parts of dichloromethane. After stirring overnight at room temperature, the reaction mixture was evaporated. The residue was partitioned between water and trichloromethane. The organic layer was dried, filtered and evaporated, yielding 5.3 parts (94.8%) of 3-chloro-6-[4-(2-chloroethyl)-1-piperidinyl]pyridazine (interm. 35).

In a similar manner there were also prepared:
3-chloro-6-[4-(3-chloropropyl)-1-piperidinyl]pyridazine (interm. 36);
3-[4-(2-chloroethyl)-1-piperidinyl]-6-methylpyridazine (interm. 37);
4-(2-chloroethyl)-1-(6-chloro-3-pyridazinyl)hexahydro-1H-azepine (interm. 38);
3-chloro-6-[4-(2-chloroethyl)-3-methyl-1-piperidinyl]-pyridazine (interm. 39).

EXAMPLE 12 a) A mixture of 7.5 parts of ethyl 3-(2-hydroxyethyl)-8-azabicyclo[3.2.1]octane-8-carboxylate (prepared as in EP-A-0,320,032) and 127 parts of hydrochloric acid was refluxed for ½ hour and was then evaporated. The residue was taken up in water and the whole was basified with NaOH. The product was extracted with trichloromethane and the extract was washed, dried, filtered and evaporated, yielding 5.1 parts (99.6%) of 8-azabicyclo[3.2.1]octane-3-ethanol (interm. 40).

b) A mixture of 5 parts of 3,6-dichloropyridazine, 5.1 parts of intermediate 40;3.5 parts of sodium carbonate and 188 parts of N,N-dimethylformamide was stirred over weekend at 60° C. After cooling, the reaction mixture was poured into water. The product was extracted with methylbenzene and the extract was washed with water, dried, filtered and evaporated. The residue was purified by column chromatography (silica gel; CHCl₃/CH₃OH 97:3). The eluent of the desired fraction was evaporated, yielding 5.1 parts (57.7%) of 8-(6-chloro-3-pyridazinyl)-8-azabicyclo[3.2.1]octane-3-ethanol (interm. 41).

In a similar manner there was also prepared:
8-(6-methyl-3-pyridazinyl)-8-azabicyclo[3.2.1]octan-3-ethanol (interm. 42).

c) To a cooled (ice-bath) mixture of 4.8 parts of thionyl chloride and 66 parts of dichloromethane there was added dropwise a solution of 5.1 parts of intermediate 41 in 200 parts of dichloromethane. After stirring overnight at room temperature, the reaction mixture was washed with NH₄OH (dil.), dried, filtered and evaporated, yielding 4.3 parts (79.1%) of 3-(2-chloroethyl)-8-(6-chloro-3-pyridazinyl)-8-azabicyclo[3.2.1]-octane (interm. 43).

In a similar manner there was also prepared:
3-(2-chloroethyl)-8-(6-methyl-3-pyridazinyl)-8-azabicyclo[3.2.1]octane (interm. 44).

EXAMPLE 13 a) A mixture of 25.9 parts of cis-3-methoxy-1-(phenylmethyl)-4-piperidineethanol (prepared as in EP-A-0,320,032) and 198 parts of methanol was hydrogenated at normal pressure and 50° C. with 3 parts of palladium-on-charcoal catalyst 10%. After the calculated amount of hydrogen was taken up, the catalyst was filtered off and the filtrate was evaporated, yielding 16.5 parts (100%) of cis-3-methoxy-4-piperidineethanol (interm. 45).

b) A mixture of 7.7 parts of 3-chloro-6-methylpyridazine, 8.5 parts of intermediate 45 and 6.4 parts of sodium carbonate was stirred overnight at 140° C. The reaction mixture was partitioned between water and dichloromethane. The organic layer was separated, dried, filtered and evaporated. The residue was purified by column chromatography (silica gel; CHCl₃/CH₃OH 97:3). The eluent of the desired fraction was evaporated, yielding 8.5 parts (63.8%) of cis-3-methoxy-1-(6-methyl-3-pyridazinyl)-4-piperidineethanol (interm. 46).

In a similar manner there were also prepared:
1-(6-methyl-3-pyridazinyl)-3-pyrrolidineethanol (interm. 47) and
1-(6-methyl-3-pyridazinyl)-3-piperidineethanol (interm. 48).

c) To a stirred and cooled (ice-bath) mixture of 8 parts of thionyl chloride and 66 parts of dichloromethane there was added dropwise a solution of 8.5 parts of intermediate 46 in 133 parts of dichloromethane. Stirring was continued overnight. The reaction mixture was evaporated and the residue was partitioned between NH₄OH (dil.) and dichloromethane. The organic layer was separated, dried, filtered and evaporated, yielding 8.1 parts (88.3%) of 3-[4-(2-chloroethyl)-3-methoxy-1-piperidinyl]-6-methylpyridazine (interm. 49).

EXAMPLE 14 a) To a stirred mixture of 67 parts of 4-piperidinemethanol, 61 parts of N,N-diethylethanamine and 750 parts of trichloromethane there were added dropwise 64.5 parts of ethyl chloroformate. Stirring was continued for 2 hours at reflux temperature. After cooling, the reaction mixture was washed with water, dried, filtered and evaporated, yielding 75 parts (70%) of ethyl 4-(hydroxymethyl)-1-piperidinecarboxylate (interm. 50).

b) To a stirred and cooled (ice-bath) solution of 46 parts of intermediate 50 in 450 parts of trichloromethane there were added dropwise 60 parts of thionyl chloride. After stirring overnight at 20° C., the reaction mixture was evaporated. The residue was coevaporated with methylbenzene, yielding 48 parts (93.3%) of ethyl 4-(chloromethyl)-1-piperidinecarboxylate (interm. 51).

c) A mixture of 10.3 parts of intermediate 51 and 190.5 parts of hydrochloric acid was stirred for 45 min at reflux temperature. After cooling, the reaction mixture was evaporated, yielding 8.6 parts (100%) of a mixture of 3-(2-chloroethyl)pyrrolidine hydrochloride and 4-(chloromethyl)piperidine hydrochloride (2:1) (interm. 52).

d) A mixture of 8.9 parts of 3,6-dichloropyridazine, 8.6 parts of intermediate 52; 21.2 parts of sodium carbonate and 235 parts of N,N-dimethylformamide was stirred overnight at 65° C. The reaction mixture was poured into ice-water and the product was extracted with dichloromethane. The extract was dried, filtered and evaporated, yielding 12.2 parts (99.1%) of a mixture of 3-chloro-6-[3-(2-chloroethyl)-1-pyrrolidinyl]-pyridazine and 3-chloro-6-(4-chloromethyl-1-piperidinyl)-pyridazine (2:1) (interm. 53).

EXAMPLE 15

To a stirred and cooled (ice-bath) mixture of 7.1 parts of thionyl chloride and 66 parts of dichloromethane there was added dropwise a solution of 6.2 parts of intermediate 33 in 200 parts of dichloromethane. Stirring was continued overnight at room temperature. The reaction mixture was evaporated and the residue was partitioned between NH$_4$OH and dichloromethane. The organic layer was separated, dried, filtered and evaporated, yielding 5.2 parts (76.8%) of a mixture of 3-[3-(2-chloroethyl)-1-pyrrolidinyl]-6-methylpyridazine and 3-(4-chloromethyl-1-piperidinyl)-6-methylpyridazine (1:1) (interm. 54).

EXAMPLE 16

To a stirred and cooled (0° C.) mixture of 25.2 parts of ethanethiol and 39.9 parts of dichloromethane there were added 12 parts of aluminumtrichloride. The solution was allowed to warm to room temperature and then there were added 6.1 parts of 4-ethyl-5-(4-methoxyphenyl)isoxazole. Stirring at room temperature was continued overnight. The reaction mixture was poured into a mixture of ice-water and hydrochloric acid. The precipitate* was filtered off and the organic layer of the filtrate was separated, dried, filtered and evaporated, yielding a first fraction of the product. The precipitate* was dissolved in a KOH (dil.). After extraction with 2,2'-oxybispropane, the aqueous layer was acidified and a second fraction of product was filtered off. Total yield: 5.6 parts (98.6%) of 4-(4-ethyl-5-isoxazolyl)-phenol (interm. 55).

EXAMPLE 17

To a cooled (ice-bath) mixture of 9.8 parts of hydroxylamine monohydrochloride in 30 parts of water, and 119 parts of ethanol there were added dropwise 25.4 parts of sodium methoxide in methanol 30% and, after stirring for 15 min, a solution of 12 parts of 3-hydroxybutanenitrile in 79 parts of ethanol. The whole was stirred for 1 hour and refluxed overnight. After cooling, the reaction mixture was filtered and the filtrate was evaporated. The residue was dissolved in trichloromethane and this solution was dried, filtered and evaporated, yielding 11 parts (66.5%) of N,3-dihydroxybutanimidamide (interm. 56).

B. Preparation of the final compounds

EXAMPLE 18

A mixture of 2.4 parts of 3-chloro-6-methylpyridazine, 5.7 parts of intermediate 7 and 2.1 parts of sodium carbonate was stirred for 3 hours at 140° C. After cooling, the reaction mixture was partitioned between dichloromethane and water. The organic layer was separated, dried, filtered and evaporated. The residue was purified by column chromatography (silica gel; CHCl$_3$/CH$_3$OH 98:2). The eluent of the desired fraction was evaporated and the residue was crystallized from 2-propanol (2×). The product was filtered off and dried at 60° C., yielding 0.7 parts (9.4%) of 3-[4-[2-[4-(3-ethyl-1,2,4-oxadiazol-5-yl)phenoxy]ethyl]-1-piperidinyl]-6-methylpyridazine; mp. 122.0° C. (comp. 5).

EXAMPLE 19

A mixture of 3.12 parts of 3-[4-(2-chloroethyl)-1-piperidinyl]-6-methylpyridazine, 2.47 parts of 4-(5-ethyl-1,2,4-oxadiazol-3-yl)phenol, 1.38 parts of sodium carbonate and 94 parts of N,N-dimethylacetamide was stirred overnight at 110° C. After cooling, the reaction mixture was poured into water. The precipitate was filtered off, washed with water and dissolved in trichloromethane. This solution was dried, filtered and evaporated. The residue was purified by column chromatography (silica gel; CHCl$_3$/CH$_3$OH 97:3). The eluent of the desired fraction was evaporated and the residue was crystallized from 2-propanone. The product was filtered off and dried, yielding 1.7 parts (33.2%) of 3-[4-[2-[4-(5-ethyl-1,2,4-oxadiazol-3-yl)phenoxy]ethyl]-1-piperidinyl]-6-methylpyridazine; mp. 125.3° C. (comp. 6).

EXAMPLE 20

A mixture of 5.6 parts of intermediate 14; 4.8 parts of intermediate 37; 5 parts of sodium carbonate and 141 parts of N,N-dimethylformamide was stirred for 5 hours at 110° C. The reaction mixture was poured into water. The precipitate was filtered off and dissolved in dichloromethane. This solution was dried, filtered and evaporated. The residue was purified by column chromatography (silica gel; CH$_2$Cl$_2$/CH$_3$OH 98:2). The eluent of the desired fraction was evaporated and the residue was dissolved in dichloromethane. The solution was washed with NaOH 10%, dried, filtered and evaporated. The residue was crystallized from 2-propanol. The product was filtered off and dried in vacuo at 50° C., yielding 1.0 part (12.5%) of 3-[4-[2-[4-(4-ethyl-2-thiazolyl)phenoxy]ethyl]-1-piperidinyl]-6-methylpyridazine; mp. 112.6° C. (comp. 22).

EXAMPLE 21

To a cooled (10° C.) mixture of 4.4 parts of intermediate 32; 3.8 parts of intermediate 12; 7.5 parts of triphenylphosphine and 66.8 parts of tetrahydrofuran there was added dropwise a solution of 5 parts of diethyl azodicarboxylate in a small amount of tetrahydrofuran. After stirring overnight at room temperature, the reaction mixture was evaporated. The residue was purified by column chromatography (silica gel; CH$_2$Cl$_2$/CH$_3$OH 99:1). The eluent of the desired fraction was evaporated and the residue was crystallized from 2-propanol. The product was filtered off and dried in vacuo at 50° C., yielding 1.4 parts (17.8%) of 3-[4-[2-[4-(2-ethyl-4-oxazolyl)phenoxy]ethyl]-1-piperidinyl]-6-methylpyridazine; mp. 123.6° C. (comp. 21).

EXAMPLE 22

To a suspension of 0.85 parts of a sodium hydride dispersion 50% and 44.5 parts of tetrahydrofuran there were added dropwise 1.95 parts of N-hydroxyhexanimidamide and, after stirring for 1 hour at room temperature, a solution of 5.1 parts of intermediate 27 in 44.5 parts of tetrahydrofuran. Stirring was continued overnight at reflux temperature. The reaction mixture was evaporated and the residue was stirred in water for ½ hour. The precipitate was filtered off, washed with water, and dissolved in dichloromethane. This solution was dried, filtered and evaporated and the residue was crystallized from 2,2'-oxybispropane. The product was filtered off and dried in vacuo at 50° C., yielding 2.7 parts (41.3%) of 3-methyl-6-[4-[2-[4-(3-pentyl-1,2,4- oxadiazol-5-yl)phenoxy]ethyl]-1-piperidinyl]pyridazine; mp. 111.1° C. (comp. 12).

EXAMPLE 23

A mixture of 3.1 parts of N-hydroxy-2-methylpropanimidamide, 2.0 parts of sodiumethoxide and 79 parts of ethanol was stirred for 15 min. There were added 5.1 parts of intermediate 27 and stirring was continued overnight at reflux temperature. The reaction mixture was evaporated and the residue was partitioned between water and dichloromethane. The organic layer was separated, dried, filtered and evaporated and the residue was crystallized from 2-propanol. The product was filtered off, washed with 2-propanol and 2,2'-oxybispropane and dried at 60° C., yielding 1.7 parts (27.8%) of 3-methyl-6-[4-[2-[4-(3-(1-methylethyl)-1,2,4-oxadiazol-5-yl)phenoxy]ethyl]-1-piperidinyl]pyridazine; mp. 135.1° C. (comp. 10).

In a similar manner there was also prepared 3-[4-[2-[4-(3-cyclopropyl-1,2,4-oxadiazol-5-yl)phenoxy]ethyl]-1-piperidinyl]-6-methylpyridazine, using sodiummethoxide instead of sodiumethoxide; mp. 143.8° C. (comp. 7).

The compounds listed in Tables 1, 2, 3 and 4 hereinbelow were prepared in a similar manner as the examples referred to in the column Ex. No.

TABLE 1

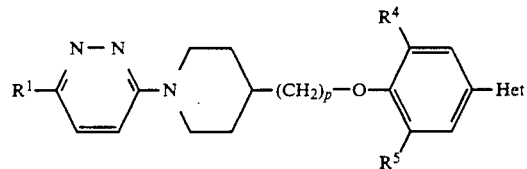

| Comp. No. | Ex. No. | $R^1$ | p | $R^4$ | $R^5$ | Het | Physical data |
|---|---|---|---|---|---|---|---|
| 1 | 19 | $CH_3$ | 2 | H | H | 3-ethyl-1,2,4-oxadiazol-5-yl | 135.0° C. |
| 2 | 19 | Cl | 2 | H | H | 3-ethyl-1,2,4-oxadiazol-5-yl | 153.3° C. |
| 3 | 19 | Cl | 3 | H | H | 3-ethyl-1,2,4-oxadiazol-5-yl | 154.1° C. |
| 4 | 19 | $CH_3$ | 3 | H | H | 3-ethyl-1,2,4-oxadiazol-5-yl | 151.1° C. |
| 5 | 18 | $CH_3$ | 2 | H | H | 3-ethyl-1,2,4-oxadiazol-5-yl (isomer) | 122.0° C. |
| 6 | 19 | $CH_3$ | 2 | H | H | 3-ethyl-1,2,4-oxadiazol-5-yl (isomer) | 125.3° C. |
| 7 | 23 | $CH_3$ | 2 | H | H | 3-cyclopropyl-1,2,4-oxadiazol-5-yl | 143.8° C. |
| 8 | 22 | $CH_3$ | 2 | H | H | 3-tert-butyl-1,2,4-oxadiazol-5-yl | 138.1° C. |
| 9 | 22 | $CH_3$ | 2 | H | H | 3-methyl-1,2,4-oxadiazol-5-yl | 132.9° C. |

TABLE 1-continued
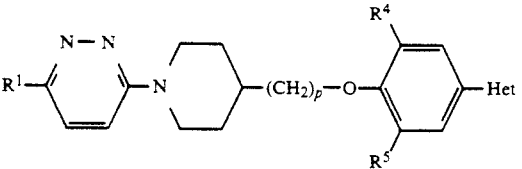
| Comp. No. | Ex. No. | R¹ | p | R⁴ | R⁵ | Het | Physical data |
|---|---|---|---|---|---|---|---|
| 10 | 23 | CH₃ | 2 | H | H | 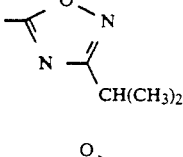 | 135.1° C. |
| 11 | 22 | CH₃ | 2 | H | H | 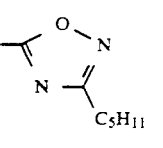 | 106.6° C. |
| 12 | 22 | CH₃ | 2 | H | H | 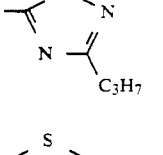 | 111.1° C. |
| 13 | 22 | CH₃ | 2 | H | H | 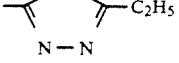 | 118.1° C. |
| 14 | 20 | CH₃ | 2 | H | H | 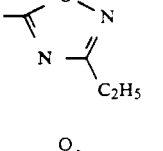 | 138.7° C. |
| 15 | 20 | Cl | 2 | H | H | 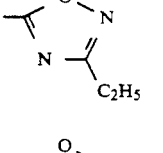 | 142.9° C. |
| 16 | 21 | CH₃ | 1 | H | H | 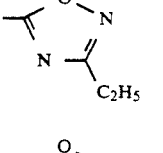 | 147.7° C. |
| 17 | 21 | Cl | 1 | H | H | 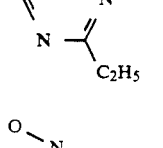 | 168.2° C. |
| 18 | 19 | Cl | 3 | H | H | 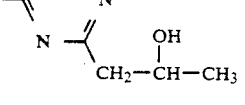 | 150.4° C. |
| 19 | 23 | CH₃ | 2 | H | H | (CH₂—CH(OH)—CH₃ oxadiazole) | 126.6° C. |

TABLE 1-continued
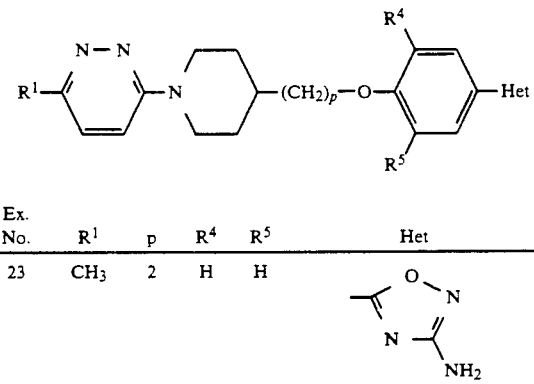
| Comp. No. | Ex. No. | R¹ | p | R⁴ | R⁵ | Het | Physical data |
|---|---|---|---|---|---|---|---|
| 20 | 23 | CH₃ | 2 | H | H | 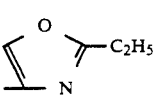 | 209.6° C. |
| 21 | 21 | CH₃ | 2 | H | H | 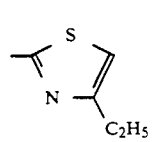 | 123.6° C. |
| 22 | 20 | CH₃ | 2 | H | H | 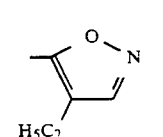 | 112.6° C. |
| 23 | 21 | CH₃ | 2 | H | H | 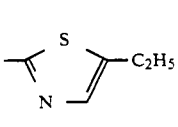 | 99.3° C. |
| 24 | 21 | CH₃ | 2 | H | H | 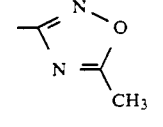 | 155.9° C. |
| 25 | 20 | CH₃ | 2 | H | H | 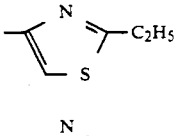 | 170.4° C. |
| 26 | 21 | CH₃ | 2 | H | H | 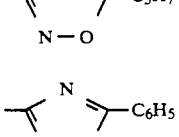 | 113.9° C. |
| 27 | 19 | CH₃ | 2 | H | H | 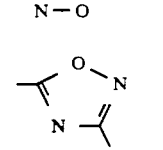 | 122.7° C. |
| 28 | 21 | CH₃ | 2 | H | H |  | 160.6° C. |
| 29 | 20 | CH₃ | 2 | Cl | Cl | | 136.8° C. |
| 30 | 21 | CH₃ | 3 | H | H | 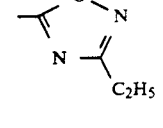 | 142.9° C. |

TABLE 1-continued
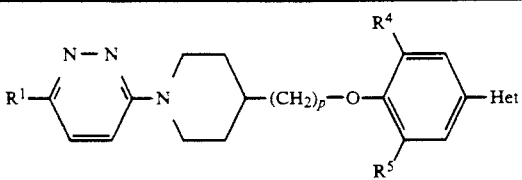
| Comp. No. | Ex. No. | R¹ | p | R⁴ | R⁵ | Het | Physical data |
|---|---|---|---|---|---|---|---|
| 31 | 20 | CH₃ | 2 | Cl | H | 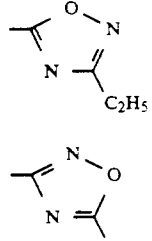 | 116.1° C. |
| 32 | 20 | CH₃ | 2 | Cl | Cl | 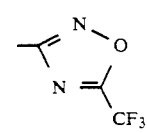 | 123.6° C. |
| 33 | 21 | CH₃ | 2 | H | H | 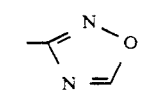 | 138.9° C. |
| 34 | 21 | CH₃ | 2 | H | H | 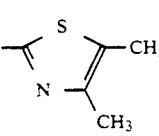 | 171.4° C. |
| 35 | 21 | CH₃ | 2 | H | H | 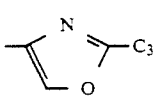 | 175.9° C. |
| 36 | 21 | CH₃ | 2 | H | H | 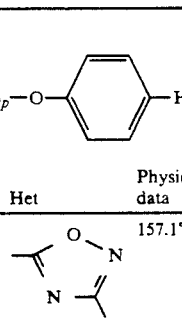 | 99.8° C. |
TABLE 2
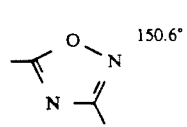
| Comp. No. | Ex. No. | R¹ | R | X | p | Het | Physical data |
|---|---|---|---|---|---|---|---|
| 37 | 20 | Cl | H | N | 3 | 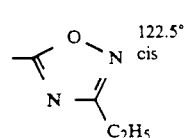 | 157.1° C. |
| 38 | 22 | Cl | H | N | 2 | 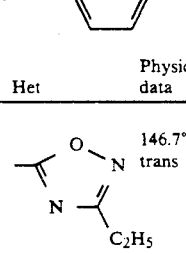 | 150.6° C. |
| 39 | 21 | Cl | CH₃ | CH | 2 | 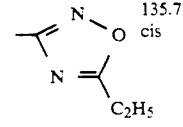 | 122.5° C. cis |
| 40 | 21 | Cl | CH₃ | CH | 2 | 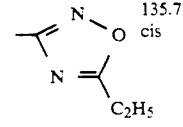 | 146.7° C. trans |
| 41 | 20 | Cl | CH₃ | CH | 2 | 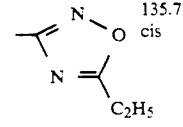 | 135.7° C. cis |

TABLE 2-continued

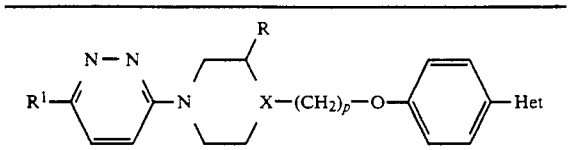

| Comp. No. | Ex. No. | R¹ | R | X | p | Het | Physical data |
|---|---|---|---|---|---|---|---|
| 42 | 20 | CH₃ | OCH₃ | CH | 2 | 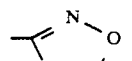 | 120.1° C. cis |
| 43 | 20 | CH₃ | OCH₃ | CH | 2 |  | 132.1° C. cis |

TABLE 3

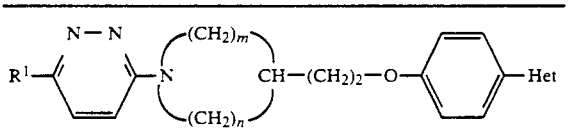

| Comp. No. | Ex. No. | R¹ | n | m | Het | Physical data |
|---|---|---|---|---|---|---|
| 44 | 20 | Cl | 2 | 1 | 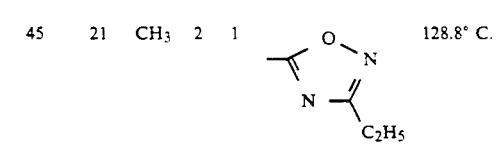 | 152.5° C. |
| 45 | 21 | CH₃ | 2 | 1 | 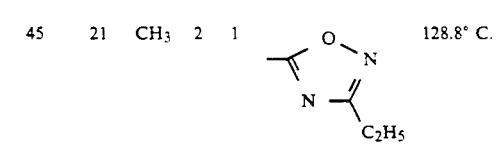 | 128.8° C. |
| 46 | 20 | CH₃ | 2 | 1 | 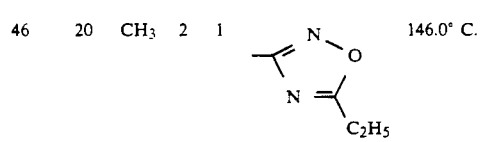 | 146.0° C. |
| 47 | 20 | Cl | 2 | 3 | 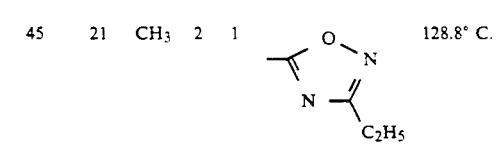 | 135.0° C. |
| 48 | 21 | CH₃ | 1 | 3 | 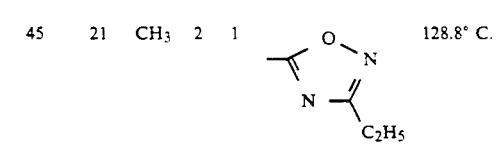 | 194.5° C./HCl |
| 49 | 21 | CH₃ | 1 | 3 | 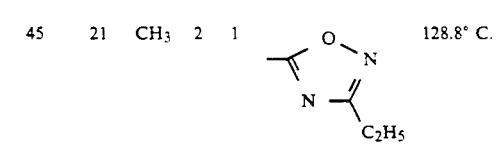 | 123.5° C./HCl ½H₂O |

TABLE 3-continued

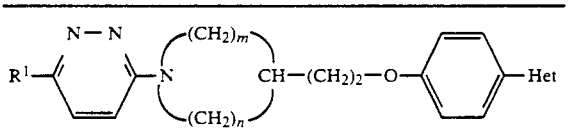

| Comp. No. | Ex. No. | R¹ | n | m | Het | Physical data |
|---|---|---|---|---|---|---|
| 50 | 20 | Cl | 2 | 3 | 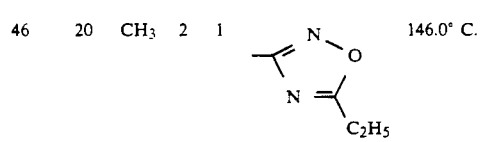 | 131.2° C. |

TABLE 4

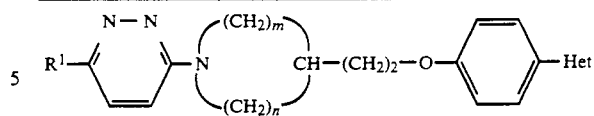

| Comp. No. | Ex. No. | R¹ | Het | Physical data |
|---|---|---|---|---|
| 51 | 19 | CH₃ |  | 155.0° C. |
| 52 | 19 | Cl |  | 165.5° C. |
| 53 | 19 | Cl | 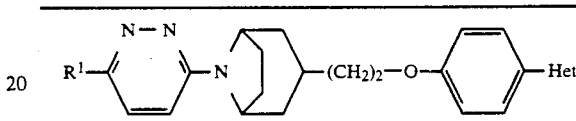 | 164.4° C. |
| 54 | 19 | CH₃ | 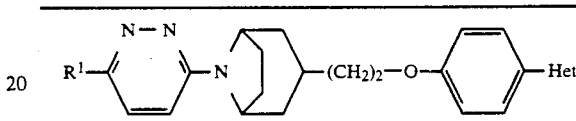 | 147.4° C. |

C. BIOLOGICAL EXAMPLES

The strong antiviral activity of the compounds of formula (I) is clearly evidenced by the data obtained in the following experiment, which data are only given to illustrate the useful antiviral properties of all the compounds of formula (I) and not to limit the invention either with respect to the scope of susceptible viruses nor with respect to the scope of formula (I).

EXAMPLE 24

Picornavirus Minimal Inhibitory Concentration Test.

The Minimal Inhibitory Concentration of the compounds of the present invention against the Human Rhinovirus strains (HRV) -2, -9, -14, -15, -29, -39, -41, -42, -45, -51, -59, -63, -70, -72, -85, -86 and -89 was determined by a standard cytopathic effect reduction assay as follows. To each of the ninety six (96) wells of a microtiter 96 well tissue culture plate there was added 60 μl of an Ohio Hela cell maintenance medium [Eagle's Basal medium supplemented with 5% Foetal Calf Serum (FCS)]. To two wells there was added 60 μl of an appropriate starting dilution of a compound of formula (I) and two-fold dilutions were made to cover a wide range of compound concentrations. Subsequently there were added 120 μl of an infectious solution of virus in Eagle's Basal Medium with 2% Hepes buffer, 2% FCS and 30 mM $MgCl_2$ to all wells except cell and compound controls. Said infectious virus solution has a $TCID_{50}$-value (Tissue Culture Infectious Dose) of about 100.

The $TCID_{50}$-value is the dose of viruses which initiates a cytopathic effect in 50% of the inoculated cells. 150 μl of the thus obtained virus-compound mixtures were then transferred to microtitre plates with subconfluent Ohio Hela Cells, grown in 100 μl of maintenance medium. Appropriate virus controls, cell controls and compound controls were included in each test. Plates were incubated for 3 to 5 days at 33° C. in 5% $CO_2$ atmosphere. They were checked daily by light microscopy without staining and read when the virus controls showed 100% cytopathic effect (CPE) and the virus back titration confirmed that a $TCID_{50}$-value between 32 and 256 had been used in the test. The $IC_{50}$-value for each virus-compound series was taken as the concentration in ng/ml that protected 50% of the cells from cytopathic effects with respect to the untreated controls. In the standard test procedure, the compounds were tested against two panels of rhinoviruses, a first panel consisting of serotypes HRV- 2, -29, -39, -85, -9, -15, -51, -59, -63, -89, -41 and the other panel consisting of HRV-42, -45, -14, -70, -72 and -86.

The $IC_{50}$-value for each rhinovirus serotype was determined, and the efficacy of each compound was determined in terms of the $Med_1$-value and $Med_2$-value, which is the medium value of the $IC_{50}$-values of all serotypes from the first and second panel respectively. The following table gives the testing results with the compounds of the invention.

| Activity of antirhinoviral compounds | | |
|---|---|---|
| Comp. No. | $Med_1$ (ng/ml) | $Med_2$ (ng/ml) |
| 1 | 6 | 44 |
| 5 | 2.9 | 98 |
| 6 | 1.3 | 47 |
| 9 | 4 | 18 |
| 11 | 6 | 175 |
| 13 | 6.8 | 154 |
| 16 | 2 | 83 |
| 38 | 2.4 | 72 |
| 21 | <0.5 | 20 |
| 22 | 1 | 203 |
| 25 | 8 | 105 |
| 44 | 14 | 166 |
| 26 | 5 | >125 |
| 27 | 6 | 122 |
| 45 | 6 | 65 |
| 46 | 5 | 40 |
| 36 | 7 | >125 |

D. COMPOSITION EXAMPLES

The following formulations exemplify typical pharmaceutical compositions in dosage unit form suitable for systemic or topical administration to warm-blooded animals in accordance with the present invention.

"Active ingredient" (A.I.) as used throughout these examples relates to a compound of formula (I), a pharmaceutically acceptable acid addition salt or a stereochemically isomeric form thereof.

EXAMPLE 25

Oral drops 500 g of the A.I. is dissolved in 0.5 l of 2-hydroxypropanoic acid and 1.5 l of the polyethylene glycol at 60°~80° C. After cooling to 30°~40° C. there are added 35 l of polyethylene glycol and the mixture is stirred well. Then there is added a solution of 1750 g of sodium saccharin in 2.5 l of purified water and while stirring there are added 2.5 l of cocoa flavor and polyethylene glycol q.s. to a volume of 50 l, providing an oral drop solution comprising 10 mg/ml of the A.I. The resulting solution is filled into suitable containers.

EXAMPLE 26

Oral solutions 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 20 g of the A.I. The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the A.I. per teaspoonful (5 ml). The resulting solution is filled in suitable containers.

EXAMPLE 27

Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

EXAMPLE 28

Film-coated tablets

Preparation of tablet core

A mixture of 100 g of the A.I., 570 g lactose and 200 g starch is mixed well and thereafter humidified with a solution of 5 g sodium dodecyl sulfate and 10 g polyvinylpyrrolidone (Kollidon-K 90 ®) in about 200 ml of water. The wet powder mixture is sieved, dried and sieved again. Then there are added 100 microcrystalline cellulose (Avicel ®) and 15 g hydrogenated vegetable oil (Sterotex ®). The whole is mixed well and compressed into tablets, giving 10.000 tablets, each comprising 10 mg of the active ingredient.

Coating

To a solution of 10 g methyl cellulose (Methocel 60 HG ®) in 75 ml of denaturated ethanol there is added a solution of 5 g of ethyl cellulose (Ethocel 22 cps ®) in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension (Opaspray K-1-2109 ®) and the whole is homogenated. The tablet cores are coated with the thus obtained mixture in a coating apparatus.

EXAMPLE 29

Injectable solutions 1.8 g methyl 4-hydroxybenzoate and 0.2 g propyl 4-hydroxybenzoate are dissolved in about 0.5 l of boiling water for injection. After cooling to about 50° C. there are added while stirring 4 g lactic acid, 0.05 g propylene glycol and 4 g of the A.I. The solution is cooled to room temperature and supplemented with water for injection q.s. ad 1 l volume, giving a solution of 4 mg A.I. per ml. The solution is sterilized by filtration (U.S.P. XVII p. 811) and filled in sterile containers.

EXAMPLE 30

Suppositories 3 g A.I. is dissolved in a solution of 3 g 2,3-dihydroxybutanedioic acid in 25 ml polyethylene glycol 400. 12 g surfactant (SPAN ®) and triglycerides (Witepsol 555 ®) q.s. ad 300 g are molten together. The latter mixture is mixed well with the former solution. The thus obtained mixture is poured into moulds at a temperature of 37°–38° C. to form 100 suppositories each containing 30 mg of the A.I.

EXAMPLE 31

Aerosols a) To a solution of 0.1 g of hydroxypropyl β-cyclodextrin (MS=0.43) in 0.7 ml of distilled water there are added 730 μg of a 0.1N hydrochloric acid solution and 2.5 mg A.I. After stirring for 10 minutes at room temperature, the pH of the thus obtained solution is adjusted to pH 5.5 by adding a 0.1N sodium hydroxide solution. Then there are added successively 4 mg of sodium chloride and 0.15 mg of phenylmercuric acetate and the whole is stirred to produce a complete solution. Distilled water is then added to a volume of 1.0 ml. The solution is filled in a glass bottle closed with a mechanical pump delivering 0.1 ml per puff upon administration.

b) To a solution of 0.1 g of dimethyl β-cyclodextrin in 0.7 ml of distilled water there are added 600 μg of a 0.1N hydrochloric acid solution and 2 mg A.I. After stirring for 10 minutes at room temperature, 10 mg of polyvinylalcohol is dissolved in the mixture and the pH of the thus obtained solution is adjusted to pH 5.5 by adding a 0.1N sodium hydroxide solution. Then there are added successively 4 mg of sodium chloride and 2 mg of phenylethyl alcohol and the whole is stirred to produce a complete solution. Distilled water is added to produce a volume of 1.0 ml which is filled in a glass bottle closed with a mechanical pump spray delivering 0.1 ml per puff upon administration.

We claim:

1. A compound of the formula:

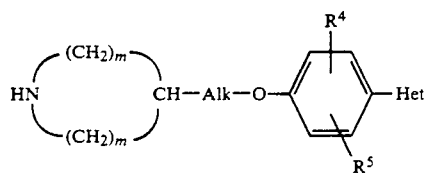

an acid addition salt or a stereochemically isomeric form thereof, wherein:

one or two carbon atoms of the $CH_2$ groups of the

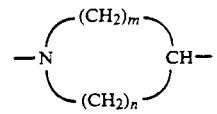

moiety may be substituted with $C_{1-4}$alkyl or $C_{1-4}$alkyloxy;

m and n each independently represent 1, 2, 3, or 4 with the sum of m and n being 3, 4 or 5;

Alk represents $C_{1-4}$alkanediyl;

$R^4$ and $R^5$ each independently represent hydrogen, $C_{1-4}$alkyl or halo; and Het represents a group of the formula:

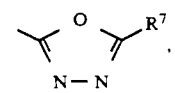 (a)

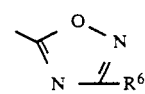 (b)

or

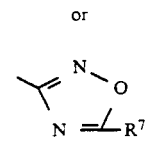 (c)

wherein:

$R^6$ represents hydrogen; $C_{1-6}$alkyl; hydroxy$C_{1-6}$alkyl; $C_{3-6}$cycloalkyl; aryl; aryl$C_{1-4}$alkyl; $C_{1-4}$alkyloxy$C_{1-4}$alkyl; $C_{3-6}$cycloalkyl$C_{1-4}$alkyl; trifluoromethyl or amino; and each $R^7$ independently represents hydrogen; $C_{1-6}$alkyl; $C_{3-6}$cycloalkyl; aryl; aryl$C_{1-4}$alkyl; $C_{1-4}$alkyloxy$C_{1-4}$alkyl; $C_{3-6}$cycloalkyl$C_{1-4}$alkyl or trifluoromethyl, wherein each aryl independently represents phenyl or phenyl substituted with 1 or 2 substituents each independently selected from halo, $C_{1-4}$alkyl, trifluoromethyl, $C_{1-4}$alkyloxy or hydroxy.

2. A compound according to claim 1 wherein m is 1, 2 or 3 and n is 1 or 2 with the sum of m and n being 3, 4 or 5, and $R^4$ and $R^5$ are each independently hydrogen or halo.

3. A compound according to claim 2 wherein in radicals (a), (b), and (c) $R^6$ or $R^7$ is $C_{1-4}$alkyl, trifluoromethyl, phenyl, $C_{3-6}$cycloalkyl, or amino.

4. A compound according to claim 3 wherein Alk is methanediyl, ethanediyl or propanediyl, m is 1 or 2 and n is 2, $R^4$ and $R^5$ are hydrogen or chloro, and in radicals (a), (b), and (c) $R^6$ or $R^7$ is ethyl or trifluoromethyl.

5. A compound according to claim 4 wherein m and n are both 2, $R^4$ and $R^5$ are hydrogen, and in radicals (a), (b), and (c) $R^6$ or $R^7$ is ethyl.

6. A compound according to claim 3 wherein the $CH_2$ groups of the

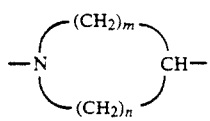

moiety are unsubstituted.

7. A compound according to claim 6 wherein Alk is ethanediyl and Het is a radical of formula (a) wherein $R^7$ is ethyl, or Het is a radical of formula (b) wherein $R^6$ is methyl, ethyl or butyl, or Het is a radical of formula (c) wherein $R^7$ is methyl, ethyl or propyl.

8. A compound according to claim 1 wherein said compound is:

4-[2-[4-(3-ethyl-1,2,4-oxadiazol-5-yl)phenoxy]ethyl]-piperidine.

* * * * *